United States Patent
Williams et al.

(10) Patent No.: US 7,083,979 B1
(45) Date of Patent: *Aug. 1, 2006

(54) METHODS FOR ENHANCED RETROVIRAL-MEDIATED GENE TRANSFER

(75) Inventors: David A Williams, Indianapolis, IN (US); Vikram P Patel, Germantown, MD (US)

(73) Assignee: Indiana University Foundation, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/394,867

(22) Filed: Sep. 13, 1999

Related U.S. Application Data

(63) Continuation of application No. 08/536,891, filed on Sep. 29, 1995, now Pat. No. 6,033,907, which is a continuation-in-part of application No. PCT/US95/03817, filed on Mar. 27, 1995, which is a continuation-in-part of application No. 08/218,355, filed on Mar. 25, 1994, now Pat. No. 5,686,278.

(51) Int. Cl.
  *C12N 15/63* (2006.01)
  *C12N 15/00* (2006.01)
  *C12P 21/06* (2006.01)
  *A01N 63/00* (2006.01)
  *C07H 1/00* (2006.01)

(52) U.S. Cl. ............... 435/455; 435/456; 435/69.1; 435/372; 435/320.1; 424/93.2; 530/350; 530/300

(58) Field of Classification Search ........... 424/93.21, 424/93.2; 514/45; 536/23.1; 435/320.1, 435/455, 369, 325
See application file for complete search history.

(56) References Cited

U.S. PATENT DOCUMENTS

| | | | |
|---|---|---|---|
| 4,727,059 A | | 2/1988 | Binder |
| 4,839,464 A | | 6/1989 | McCarthy |
| 4,980,279 A | | 12/1990 | Peters |
| 5,004,681 A | | 4/1991 | Boyse |
| 5,019,646 A | | 5/1991 | Furcht |
| 5,102,988 A | | 4/1992 | Kimizuka |
| 5,116,368 A | | 5/1992 | McCarthy |
| 5,124,155 A | | 6/1992 | Reich |
| 5,175,096 A | | 12/1992 | Hook |
| 5,188,959 A | | 2/1993 | Haberman |
| 5,198,423 A | | 3/1993 | Taguchi et al. |
| 5,229,172 A | | 7/1993 | Cahalan et al. |
| 5,299,172 A | | 3/1994 | Badger |
| 5,354,686 A | * | 10/1994 | Haberman ............... 435/240.2 |
| 5,405,772 A | * | 4/1995 | Ponting ................ 435/240.31 |
| 5,409,825 A | | 4/1995 | Hoffman |
| 5,670,351 A | * | 9/1997 | Emerson et al. ......... 435/172.3 |
| 5,686,278 A | * | 11/1997 | Williams et al. ......... 435/172.3 |
| 6,033,907 A | * | 3/2000 | Williams .................... 435/325 |
| 6,051,427 A | * | 4/2000 | Finer et al. ................. 435/369 |

FOREIGN PATENT DOCUMENTS

| | | |
|---|---|---|
| EP | 0 349 342 A2 | 1/1990 |
| EP | 0 399 806 A1 | 1/1990 |
| JP | 2 311498 | 12/1989 |
| JP | 2 97397 | 9/1990 |
| WO | WO 90/13641 | 11/1990 |
| WO | WO 93/18137 A1 | 9/1993 |
| WO | WO 94/02610 | 2/1994 |
| WO | WO 95/26200 | 10/1995 |

OTHER PUBLICATIONS

AN 1999219789, Medline, Gene therapy.*
Kohn, MD, The current status of gene therapy using hematopietic stem cells, 1995, Current Science in Pediatrics, vol. 5, pp. 56-63.*
Moritz et al., Bone Marrow Extracelluar Matrix Molecules Improve Gene Transfer in Human Hematopoietic Cells via Retroviral Vectors, Apr. 1994, J. Clin. Invest., vol. 93, pp. 1451-1457.*
Moritz et al., Human Cord Blood Cells as Targets for Gene Transfer: Potential Use in Genetic Therapies of Severe Combined Immunodeficiency Disease, Aug. 1993, vol. 178, pp. 529-536.*
Williams et al., Umbilical Cord Blood Stem Cells as Targets for Genetic Modification: New Therapeutic Approaches to Somatic Gene therapy, 1994, Blood Cells, vol. 20, pp. 504-516.*
Riddell et al., T-cell medicated rejection of gene-modified HIV-specific cytotoxic T lymphocytesa in HIV-infected patients, Feb. 1996, Nature, vol. 2, No. 2, pp. 216-223.*
Anderson, Human gene therapy, Apr. 30, 1998, Nature, vol. 392, pp. 25-30.*
Verma et al., Gene therapy-promises, problems and prospects, Sep. 18, 1997, Nature, vol. 389, pp. 239-242.*
Ngo et al., Computational Complexity Protein Structure Prediction, and the Levinthal Paradox, 1994, Birkhauser Boston, pp. 492-495.*
Hoogerburgg et al., Bone marrow gene transfer in three patients with adeosine deaminase deficiency, 1993, Gene Therapy, vol. 3, pp. 179-183.*
AN 1999219789, Medline, Gene therapy, 1999.*

(Continued)

*Primary Examiner*—Dave Trong Nguyen
*Assistant Examiner*—Maria Marvich
(74) *Attorney, Agent, or Firm*—Woodard, Emhardt, Moriarty, McNett & Henry LLP

(57) ABSTRACT

A method to increase the efficiency of transduction of hematopoietic and other cells by retroviruses includes infecting the cells in the presence of fibronectin or fibronectin fragments. The fibronectin and fibronectin fragments significantly enhance retroviral-mediated gene transfer into the cells, particularly hematopoietic cells including committed progenitors and primitive hematopoietic stem cells. The invention also provides improved methods for somatic gene therapy capitalizing on enhanced gene transfer, hematopoietic cellular populations, and novel constructs for enhancing retroviral-mediated DNA transfer into cells and their use.

24 Claims, 20 Drawing Sheets

OTHER PUBLICATIONS

Kohn, MD, The current status of gene therapy using hematopietic stem cells, 1995, Current Science in Pediatrics, vol. 5, pp. 56-63.*

Moritz et al., Bone Marrow Extracelluar Matrix Molecules Improve Gene Transfer in Human Hematopoietic Cells via Retroviral Vectors, Apr. 1994, J. Clin. Invest., vol. 93, pp. 1451-1457.*

Moritz et al., Human Cord Blood Cells as Targets for Gene Transfer: Potential Use in Genetic Therapies of Severe Combined Immunodeficiency Disease, Aug. 1993, vol. 178, pp. 529-536.*

Verma, IM et al., "Gene therapy-promises, problems, and prospects", Nature, 1997, vol./Issue No. 389, pp. 239-242.

"Bubble Boy saved by gene therapy", BBC News, Apr. 3, 2000.

"Cell-Cell Adhesion and the Extracellular Matrix", Molecular Biology of the Cell, 1983, pp. 673-713, Garland Publishing Co., New York.

Anderson, W. French, "Prospects for Human Gene Therapy", Science, 1984, vol. 226 (4673) pp. 401-409.

Anderson, W. French, "Human Genes Therapy—SCIENCE", SCIENCE, May 8, 1992, vol./Issue No. 258, pp. 808-813.

Apperley, J.F., et al., "Retroviral Gene Transfer of Human Adenosine Deaminase in Murine Hematopoiatic Cells: Effect of Selectable Marker Sequences on Long-Term Expression", Amer. Soc. Hematology 1991 pp. 310-317.

Ashwell, G. et al., "Carbohydrate-Specific Receptors of the Liver", Ann. Rev. Biochem, 1982, vol./Issue No. 61, pp. 631-664.

Bernardi et al., "Lymphoid Precursor Cells Adhere to Two Different Sites on Fibronectin", J. Cell Biol., 1987, vol./Issue No. 106, pp. 489-498.

Bienzle, Dorothee et al., "Gene transfer into hematopoietic stem cells: Long-term maintenance on in vitro activated progenitors without marrow ablation", Proc. Natl. Acad. Sci. USA, 1994, vol./Issue No. 91, pp. 350-354.

Bodine, D.M. et al., "Long-term in vivo expression of a Murine Adenosine Deaminase Gene in Rhesus Monkey Hematopoietic Cells of Multiple Lineages After Retroviral-mediated Gene Transfer into CD34+ Bone Marrow Cells" Blood 1993 vol./Issue No. 82:7 pp. 1975-1980.

Bodine, David M., et al., "Development of a High-Titer Retrovirus Producer Cell Line Capable of Gene Transfer into Rhesus Monkey Hematopoietic Stem Cells", Proc. Natl. Acad. Sci. USA, 1990, vol./Issue No. 87, pp. 3738-3742.

Bradley, T.R. et al., "The Growth of Mouse Bone Marrow Cells in Vitro", Aust. J. Exp. Biol. Med. Sci., 1966, vol./Issue No. 44, pp. 287-300.

Broxmeyer, H.E. et al., "Umbilical Cord Blood Hematopoietic Stem and Repopulating Cells in Human Clinical Transplantation", Blood Cells, 1991, vol./Issue No. 17, pp. 313-329.

Carter, et al., "Autologous Transplantation of Canine Long-Term Marrow Culture Cells Genetically Marked by Retroviral Vectors", Blood, 1992, vol./Issue No. 79:2, pp. 356-364.

Cornetta, et al., "Protamine sulfate as an effective alternative to polybrene in retroviral-mediated gene-transfer: implications for human gene therapy", Journal of Virological Methods, 1989, vol./Issue No. 23, pp. 187-194.

Cristiano, R.J., et al., "Hepatic Gene Therapy: Adenovirus Enhancement of Receptor-Mediated Gene Delivery and Expression in Primary Hepatocytes", Proc. Natl. Acad. Sci. USA, 1993, vol./Issue No. 90, pp. 2122-2126.

Dilber, MS. et al., "Basic fibroblast growth factor increases retroviral-mediated gene transfer into human hematopoietic peripheral blood progenitor cells", Exp. Hematol, 1994, vol./Issue No. 22:12, pp. 1129-1133.

Emons, G. et al., "The Use of Luteinizing Hormone Releasing Hormone Agonists and Antagonists in Gynecological Cancers", Hum. Reprod., 1994, vol./Issue No. 9:7,pp. 1364-1379.

Fichard et al., "Another Look at Collagen V and XI Molecules", Matix Biology, 1994, vol./Issue No. 14, pp. 515-531.

Flasshove, M. et al., "Increased resistance to taxol for peripheral blood progenitor cells following transduction with an MDR1-encoding retroviral vector", Exp. Hematol., 1995, vol./Issue No. Abstract 23/8 pp. 934.

Flasshove, Michale, et al., "Ex Vivo Expansion and Selection of Human CD34+ Peripheral Blood Progenitor Cells After Introduction of a Mutated Dihydrofolate Reductase cDNA via Retroviral Gene Transfer", Blood Jan. 2, 1995 vol./Issue No. 85-2 pp. 566-574.

Friedmann, Theodore, "Progress Toward Human Gene Therapy", Science, Jun. 1989, pp. 1276-1281.

Gluckman, E. et al., "Bone Marrow Transplantation in Fanconi Anaemia", British J. of Haem., 1980, vol./Issue No. 45, pp. 557-564.

Hanenberg, A. et al., "Rapid and efficient transduction of primitive hematopholetic cells; role of retrovirus adhesion in fibronectin assisted gene transfer", Blood, 1995, vol./Issue No. 86:10, pp. 465a.

Haraguchi et al., "Effects of Polycations on Infection with Human Retroviruses", Int. Conf. AIDS, 1994, vol./Issue No. 10:2, pp. 114.

Hodgson, Clague P. et al., "Virosomes: Cationic Liposomes Enhance Retroviral Transduction", Nature Biotechnology, 1996, vol./Issue No. 14, pp. 339-342.

Hogge, Donna E. et al., "The Elusive Peripheral Blood Hemotopietic Stem Cell", Seminars in Hematology, 1993, vol./Issue No. 30:4 Supp. 4, pp. 82-89.

Hoshino, K, "Effects of polycations on infection of human retroviruses", Working Group on Structure and function of HIV,"Working Report of 1993", 1994, vol./Issue No. Partial Translation, pp. 24-27.

Howell, A. et al., "Response to a Specific Antioestrogen (ICI 182780) in Tamoxifen—Resistant Breast Cancer", The Lancet, 1995, vol./Issue No. 345, pp. 29-30.

Hows, J.M. et al. , "Growth of human umbilical cord blood in longterm haemopoietic cultures", Lancet, Jul. 11, 1992, vol./Issue No. 340, pp. 73-76.

Karlsson, Stefan, "Treatment of Genetic Defects in Hematopoietic Cell Function by Gene Transfer", Blood, 1991, vol./Issue No. 78:10, pp. 2481-2492.

Kasahara, N. et al., "Tissue-Specific Targeting of Retroviral Vectors Through Ligand-Receptor Interactions", Science, 1994, vol./Issue No. 266, pp. 1373-1376.

Kimizuka et al., "Production and Characterizaton of Functional Domains of Human Fibronectin Expressed in *Escherichia coli*", J. Biochem., 1991, vol./Issue No. 110:2, pp. 284-291.

Klijn, J.G.M. et al., "Pre-Clinical and Clinical Treatment of Breast Cancer With Antiprogestins", Hum. Reprod., 1994, vol./Issue No. 9 Supp. 1, pp. 181-189.

Kohli-Kumar, M. et al., "Haematopoietic Stem/Progenitor Cell Transplant in Fanconi Anaemia Using HLA-Matched Sibling Umbilical Cord Blood Cells", British J. Haern., 1993, vol./Issue No. 85, pp. 419-422.

Kornblihtt, A.R., et al., "Isolation and characterization of cDNA clones for humans and bovine fibronectin", Proc. Natl. Acad. Sci. USA, 1983, vol./Issue No. 80:11, pp. 3218-3222.

Kornblihtt, A.R., et al., "Human fibronectin: cell specific alternative mRNA splicing generates polypeptide chains differing in the number of internal repeats", Nucleic Acids Res., 1984, vol./Issue No. Abstract 12/14 pp. 5853-5868.

Kornblihtt, A.R., et al., "Human fibronectin: molecular cloning evidence for two mRNA species differing by an internal segment coding for a structural domain", EMBO J., 1984, vol./Issue No. Abstract 3/1 pp. 221-226.

Kornblihtt, A.R., et al., "Primary structure of human fibronectin: differential splicing may generate at least 10 polypeptides from a single gene", EMBO J., 1985, vol./Issue No. 4:7, pp. 1755-1759.

Lim, B., et al., "Retrovirus-Mediated Gene Transfer of Human Adenosine Deaminase: Expression of Functional Enzyme in Murine Hematopoietic Stem Cells in Vivo", Mol. Cell. Biol., 1987, vol./Issue No. 7:10 pp. 3459-3465.

Lim, et al., "Long-Term Expression Of Human Adenosine Deaminase In Mice Transplanted With Retrovirus-Infected Hematopoietic Stem Cells", Proc. Natl. Acad. Sci. U.S.A., 1989, vol./Issue No. 86, pp. 8892-8896.

Long, Michael W., "Blood Cell Cytoadhesion Molecules", Exp. Hematol, 1992, vol./Issue No. 20, pp. 288-301.

Lu, L. et al., "CD34 stem/progenitor cells purified from cryopreserved cord blood can be transduced with high efficiency by a retroviral vector and expanded ex vivo with stable integration and expression of fanconi anemia complement c gene" Blood 1994 vol./Issue No. Abstract 84/10 Supp. 1 pp. 355a.

Luskey, B.D., et al., "Stem Cell Factor, Interleukin-3, and Interleukin-6 Promote Retroviral-Mediated Gene Transfer Into Murine Hematopoietic Stem Cells", Blood, 1992, vol./Issue No. 80:2, pp. 396-402.

Markowitz, D. et al., "A Safe Packaging Line for Gene Transfer: Separating Viral Genes on Two Different Plasmids", J. Virol., 1988, vol./Issue No. 62:4, pp. 1120-1124.

Markowitz, D. et al., "Construction and Use of a Safe and Efficient Amphotropic Packaging Cell Line", Virology, 1988, vol./Issue No. 167, pp. 400-406.

McGlave P. et al., "Interaction of primitive human myeloid and lymphoid progenitors with the marrow microenvironment"; Blood Cells, 1994, vol./Issue No. 20:1, pp. 121-128.

Merwin, June R. et al., "Target Delivery of DNA Using YEE(GalNAcAH)3, a Synthetic Glycopeptide Ligand for the Asialoglycoprotein Receptor", Bioconjugate Chem., 1994, vol./Issue No. 5:6 pp. 612-620.

Miller, A. Dusty, "Human Gene Therapy Comes of Age", Nature, Jun. 11, 1992, vol./Issue No. 357, pp. 455-460.

Moore, Kateri A. et al., "Stromal Support Enhances Cell-Free Rectroviral Vector Transduction of Human Bone Marrow Long-Term Culture-Initiating Cells", Blood, 1992, vol./Issue No. 79:6, pp. 1393-1399.

Moore, M.A., et al., "Gene Therapy: New Frontiers, an International Symposium", Meeting Abstract: Dublin, Ireland, Sep. 18-21, 1994, pp. 1-2.

Moore, Malcolm A.S., "Ex vivo expansion of cord blood-derived stem cells and progenitors", Blood Cells, 1994, vol./Issue No. 20, pp. 468-481.

Ngo, et al., "The Protein Folding Problem and Tertiary Structure Prediction", 1994, pp. 492-495, Birkhäuser, Boston, US.

Nojima, Yoshihisa et al., "Ligation of VLA-4 on T Cells Stimulates Tyrosine Phoshorylation of a 105-kD Protein", J. Exp. Med., 1992, vol./Issue No. 175, pp. 1045-1053.

Ohashi, T., et al., "Efficient Transfer and Sustained High Expression of the Human Glucocerebrosidase Gene in Mice and Their Functional Macrophages Following Transplantation of Bone Marrow Transduced by a Retroviral Vector" Proc Natl Acad Sci Usa 1992 vol./Issue No. 89.

Patel et al., "Generation of interleukin-2 Secreting melanoma Cell Populations from Resected Metastaic Tumor", Human Gene Therapy, 1994, vol./Issue No. 5, pp. 577-584.

Patel, et al., "Loss of Adhesion of Murine Erythroleukemia Cells to Fibronectin During Erythroid Differentiation", Science, 1984, vol./Issue No. 224, pp. 996-998.

Reisbach, G. et al., "Characterization of hemopoietic cell populations from human cord blood expressing c-kit", Exp. Hematol., 1993, vol./Issue No. 21, pp. 74-79.

Ruoslahti, E., "Fibro-nectin; Purification, Immunochemical Properties, and Biological Activities", Methods in Enzymology, 1982, vol./Issue No. 82, pp. 803-831.

Ruoslahti, E., "Fibronectin and Its Receptors", Ann. Rev. Biochem., 1988, vol./Issue No. 57, pp. 375-413.

Ruoslahti, E. et al., "Alignment Of Biologically Active Domains in The Fibronectin Molecule", J. Bio. Chem., 1981, vol./Issue No. 256, pp. 7277-7281.

Saiki, Ikuo et al., "Inhibitory effect of fibronectin and its recombinant polypeptides on the adhesion of metastic melanoma cells to Laminin", Jpn. J. Cancer Res., 1991, vol./Issue No. 82, pp. 1112-1119.

Sekiguchi, K. et al., "Human Liver Fibronectin Complementary DNAs: Identification of Two Different Messenger RNAs Possibly Encoding the $\alpha$ and $\beta$ Subunits of Plasma Fibronectin", Biochemistry 1986 vol./Issue No. 25, pp. 4936-4941.

Shih, C-C., et al., "Highly Preferred Targets for Retrovirus Integration", Cell, 1988, vol./Issue No. 53, pp. 531-537.

Singh, Vinod et al., "Hormonotoxins: Preparation and Characterization of Ovine Luteinizing Hormone-Gelonin Conjugate", Journal of Biological Chemistry, 1989, vol./Issue No. 264:6, pp. 3089-3095.

Sorrentino, Brian P. et al., "Selection of Drug Resistant Bone Marrow Cells in Vivo After Retrovial Transfer of Human MDR1", SCIENCE, Jul. 3, 1992, vol./Issue No. 257, pp. 99-100.

Sutherland et al., "Characterization and Partial Purification of Human Marrow Cells Capable of Initiating Long-Term Hematopoiesis In Vitro", Blood, 1989, vol./Issue No. 74-5, pp. 1563-1570.

Toksoz et al., "Support of Human Hematopoiesis in Long-Term Bone Marrow Cultures by Muring Stromal Cells Selectively Expressing the Membrane-Bound and Secreted Forms of the Human Homolog of the Steel Gene Product Stem Cell Factor" Proc Natl Acad Sci USA 1992 vol./Issue.

Tolcher, A.W., "Current Status of Post-chemotherapy Tamoxifen in Early Breast Cancer", Oncology, Nov. 1994, vol./Issue No. 8/11, pp. 39-43.

Torre, D. et al., "Interaction of human plasma fibronectin with viral proteins of human immunodeficiency virus", Fems. Immunol. Med. Microbiol., 1994, vol./Issue No. 8-2, pp. 127-131.

Tsai, Schwickwann et al., "Differential binding of erythroid and myeloid progenitors to fibroblasts and fibronectin", Blood, 1987, vol./Issue No. 69-6, pp. 1587-1594.

Valsesia-Wittman, S. et al., "Modifications in the Binding Domain of Avian Retrovirus Envelope Protein to Redirect the Host Range of Retroviral Vectors", J. Virol., 1994, vol./Issue No. 68:7 pp. 4609-4619.

Van Beusechem. V.W., et al., "Long-Term Expression of Human Adenosine Deaminase In Rhesus Monkeys Transplanted with Retrovirus-Infected Bone-Marrow Cells", Proc. Natl. Acad. Sci. USA 1992 vol./Issue No. 89 pp. 7640-7644.

Van Der Sluijs, "Differential Adherence of Murine Hematopoietic Stem Cell Subsets to Fibronectin", Experimental Hematology, 1994, vol./Issue No. 22, pp. 1236-1243.

Varmus, Harold, "Retroviruses", SCIENCE, Jun. 10, 1988, pp. 1427-1434.

Verfaillie, C.M., et al., "Differentiation of Primitive Human Multipotent Hematopoietic Progenitors Into Single Lineage Clonogenic Progenitors is Accompanied by Alterations in Their Interaction with Fibronectin" J. Exp. Med. 1991 vol./Issue No. 174, pp. 693-703.

Wagner, J.E. et al., "Transplantation of Umbilical Cord Blood After Myeloblastive Therapy: Analysis of Engraftment", Blood, 1992, vol./Issue No. 79:7, pp. 1874-1882.

Wagner, J.E. et al., "Allogenic umbilical cord blood transplantation: Report of results in 26 patients", Blood, 1993, vol./Issue No. Abstract, pp. 82-86a.

Watt et al., "Adhesion Receptors are differentially expressed on Developing Thymocytes and Epithelium in Human Thymus", Experimental Hematology, 1992, vol./Issue No. 20, pp. 1101-1111.

Wiginton, Dan A. et al., "Complete Sequence and Structure of the Gene for Human Adenosine Deaminase", Biochemistry, 1986, vol./Issue No. 25, pp. 8234-8244.

Williams, David A. et al., "Fibronectin and VLA-4 in Haematopoistic Stem Cell-Microenvironment Interactions", Nature, 1991, vol./Issue No. 352, pp. 438-441.

Xiao, M. et al., "Extensive proliferative capacity of single isolated CD34 human cord blood cells in suspension culture", Blood Cells, vol./Issue No. 20, pp. 455-467.

Xu, L.C., et al., "Long-term in vivo expression of the human glucocerebrosidase gene in nonhuman primates after CD34+ hematopoietic cell transduction with cell-free retroviral vector preparations", Proc. Natl. Acad. Sci. USA 1995 vol./Issue No. 92 pp. 4372-4376.

Xu, Lincheng, et al., "Correction of the enzyme deficiency in hematopoietic cells of Gaucher patients using a clinically acceptable retroviral supernatant transduction protocol", Experimental Hematology 1994 vol./Issue No. 22, pp. 223-230.

Yao et al., "Primary myoblast-mediated gene transfer: persistent expression of human factor IX in mice", Gene Therapy, 1994, vol./Issue No. 1:2, pp. 99-107.

Ziegler, B.L. et al., "Phenotype analysis of umbilical cord (CB) blood CD34 cell subpopulations", Blood, 1992, vol./Issue No. 80 Supp. 1, pp. 408A.

* cited by examiner

Heparin Blocks Virus Binding to Fibronectin

FIG. 9

GENE TRANSFER INTO HL60 CELLS

SEQUENCE LISTING

<160> NUMBER OF SEQ ID NOS: 2

<210> SEQ ID NO 1
<211> LENGTH: 271
<212> TYPE: PRT
<213> ORGANISM: Homo sapiens

<400> SEQUENCE: 1

```
Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
             20                  25                  30

Arg Val Arg Val Thr Pro Lys Glu Lys Thr Gly Pro Met Lys Glu Ile
         35                  40                  45

Asn Leu Ala Pro Asp Ser Ser Val Val Ser Gly Leu Met Val
 50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu Asn Val Ser Pro
                 85                  90                  95

Pro Arg Arg Ala Arg Val Thr Asp Ala Thr Glu Thr Thr Ile Thr Ile
             100                 105                 110

Ser Trp Arg Thr Lys Thr Glu Thr Ile Thr Gly Phe Gln Val Asp Ala
             115                 120                 125

Val Pro Ala Asn Gly Gln Thr Pro Ile Gln Arg Thr Ile Lys Pro Asp
 130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                 165                 170                 175

Ile Asp Ala Ser Thr Ala Ile Asp Ala Pro Ser Asn Leu Arg Phe Leu
             180                 185                 190

Ala Thr Thr Pro Asn Ser Leu Leu Val Ser Trp Gln Pro Pro Arg Ala
             195                 200                 205

Arg Ile Thr Gly Tyr Ile Ile Lys Tyr Glu Lys Pro Gly Ser Pro Pro
         210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                 245                 250                 255

Lys Asn Asn Gln Lys Ser Glu Pro Leu Ile Gly Arg Lys Lys Thr
             260                 265                 270

<210> SEQ ID NO 2
<211> LENGTH: 25
<212> TYPE: PRT
<213> ORGANISM: Homo sapiens

<400> SEQUENCE: 2

Asp Glu Leu Pro Gln Leu Val Thr Leu Pro His Pro Asn Leu His Gly
 1               5                  10                  15

Pro Glu Ile Leu Asp Val Pro Ser Thr
             20                  25
```

METHODS FOR ENHANCED RETROVIRAL-MEDIATED GENE TRANSFER

CROSS-REFERENCE TO RELATED APPLICATIONS

This application is a continuation of U.S. patent application Ser. No. 08/536,891, filed Sep. 29, 1995, now U.S. Pat. No. 6,033,907, which is a continuation-in-part of International Application No. PCT/US95/03817 designating the United States, filed Mar. 27, 1995, which is a continuation-in-part of U.S. patent application Ser. No. 08/218,355, filed Mar. 25, 1994, now U.S. Pat. No. 5,686,278.

Part of the work during the development of this invention was made with government support under Grant Numbers PO1HL45168 and RO1 HL46528 awarded by the National Institutes of Health. The U.S. Government has certain rights in the invention.

FIELD OF THE INVENTION

The present invention relates generally to methods for increasing the efficiency of transduction of cells by viruses, and more particularly to methods for enhancing viral-mediated gene transfer into cells utilizing fibronectin and/or fibronectin fragments.

BACKGROUND OF THE INVENTION

Progress in understanding the molecular basis of many human diseases as well as improvement in gene transfer technology has led to recent attempts to develop protocols for somatic gene therapy for severe genetic diseases. Currently, promising disease candidates for human gene therapy include those in which an enzyme or other protein is defective or missing, where the level of enzyme or protein does not need to be exactly regulated, especially those that are constitutively regulated, and those defects which are found in the patient's bone marrow.

For example, one disease candidate for gene therapy is adenosine deaminase (ADA) deficiency which results in severe combined immunodeficiency disease (SCID). ADA deficient patients have little or no detectable enzyme in bone marrow cells. However, ADA deficiency has been cured by matched bone marrow transplantation. ADA normal cells have a selective advantage over ADA deficient cells and will normally repopulate the patient's bone marrow.

Bone marrow cells are a good target for somatic gene therapy because bone marrow tissue is easily manipulated in vitro and contains repopulating cells. Alternatively, human cord blood has previously also been demonstrated to contain a large number of primitive progenitor cells. Successful gene transfer into hematopoietic stem cells, the long term repopulating cells, may lead to lifelong cures for a variety of diseases manifested in the progeny of these cells.

Gene transfer into, and long term gene expression in, repopulating stem cells has been achieved in murine models by a number of investigators. However, in vivo experiments in larger animals, such as dogs and primates, have met with limited success, largely due to the low efficiency of infection of primitive hematopoietic stem cells. The limitations of current gene transfer technology are further complicated when applied to human protocols by several factors, including the low numbers of stem cells present in adult bone marrow (ABM), the lack of suitable methods to purify these cells, and the low fraction of such primitive cells in cell cycle.

In both murine and large animal experiments involving bone marrow cells, it has been noted that the most successful protocols utilize cocultivation of target cells with retroviral producer cell lines. Also, most of the FDA-approved gene transfer trials in humans rely on recombinant retroviral vectors for gene transduction. Recombinant retroviral vectors are desirable for gene therapy because they efficiently transfer and precisely and stably integrate exogenous DNA into cellular DNA. These vectors contain exogenous DNA for gene transfer and are further modified to eliminate viral pathogenicity. Because of these modifications, viral production is generally accomplished using retrovirus packaging cells. However, for clinical gene therapy, cell-free transduction is more desirable due to concerns about bio-safety and quality control. Unfortunately, efficient gene transfer into hematopoietic cells such as stem cells has generally not been possible without cocultivation with virus-producing cells.

Recently, it has been shown that gene transfer efficiency can be increased by exposing target cells to stromal cells during infection. Stromal cells are a major component of the hematopoietic microenvironment (HM). The HM consists of an organized network of macrophages, stromal cells, endothelial cells, adipocytes and a complex extracellular matrix (ECM) made up of a variety of defined adhesion molecules. ECM molecules such as laminin, collagen, thrombospondin, proteoglycans, glycosaminoglycans and fibronectin provide anchorage sites for both hematopoietic cells and growth factors. The mechanism underlying this promoting effect of stroma on retroviral infection is unclear, but it has been known for some time that physiologic regulation of the proliferation and differentiation of hematopoietic cells occurs when these cells are in direct contact with cells of the HM.

Efficient gene transfer into long term repopulating hematopoietic stem cells and other cells remains problematic, inhibiting the widespread application of gene transfer protocols for curative therapy of hematopoietic and other diseases at present. A need persists for methods for efficient transfer of genetic material into mammalian cells without the dangers and limitations of past methods. The present invention addresses these needs.

SUMMARY OF THE INVENTION

Briefly, one preferred embodiment of this invention provides a method for increasing the frequency of transduction of hematopoietic cells by a retrovirus vector. The method includes infecting viable hematopoietic cells with a replication-defective recombinant retrovirus vector in the presence of substantially pure fibronectin and/or fibronectin fragments effective to increase the frequency of cellular transduction by the retrovirus. The fibronectin and/or fibronectin fragments can be derived from naturally-occurring materials or can be synthetically derived (e.g. genetically engineered by recombinant or chemical synthesis techniques), or derived from a combination of naturally-occuring and synthetic materials. In addition, it will be understood that the fibronectin polypeptide or polypetides utilized in the invention may include mutations to the naturally-occurring fibronectin amino acid sequence which nonetheless provide functional polypeptides having the adhesion properties necessary for achieving enhanced transduction in accordance with the invention.

Another preferred embodiment of the invention provides a method for producing transduced hematopoietic cells which includes infecting viable hematopoietic cells with a replication-defective recombinant retrovirus carrying exogenous DNA in the presence of immobilized fibronectin, immobilized fibronectin fragments, or an immobilized mixture thereof in amounts effective to increase the frequency of cellular transduction by the retrovirus.

Another preferred embodiment of the invention provides an improved method for cellular grafting. The method includes the steps of obtaining viable hematopoietic cells from an animal donor; infecting the hematopoietic cells with a recombinant retrovirus vector to produce transduced viable hematopoietic cells, the infecting being in the presence of fibronectin and/or a fragment thereof in immobilized form and effective to increase the frequency of transduction; and introducing the transduced viable hematopoietic cells into an animal recipient as a cellular graft. In one preferred mode the infected cells can be introduced into an autologous donor.

Another preferred embodiment of the present invention provides a method for obtaining transduced umbilical cord blood cells suitable for a cellular engraftment procedure. The method includes infecting hematopoietic cells from umbilical cord blood with a replication-defective recombinant retrovirus vector in the presence of an effective immobilized amount of fibronectin and/or fibronectin fragments to increase the frequency of transduction of the hematopoietic cells by the retrovirus vector. The invention also includes viable transduced cellular populations from umbilical cord blood obtainable by such a method, and cellular grafting methods which include introducing the transduced cellular populations into an animal as a cellular graft.

In accordance with more specific aspects of the above-mentioned embodiments of the invention, the fibronectin or fibronectin fragment utilized will contain a first amino acid sequence which provides the retroviral-binding activity of the Heparin-II-binding domain of fibronectin, and a second amino acid sequence which provides the cell-binding activity of the CS-1 domain of fibronectin. The use of these two binding domains of fibronectin together has proven to very significantly enhance the transduction efficiency of the target cells by the retrovirus.

Another preferred embodiment of the invention provides a method for producing a construct for enhancing the frequency of transduction of a predetermined target cell by a retrovirus vector. The method includes the step of covalently coupling a ligand which binds to said target cell to a polypeptide containing an amino acid sequence which provides the retroviral-binding activity of the Heparin-II binding domain of fibronectin. The present invention also includes methods involving the utilization of these constructs to increase the frequency of transduction of the predetermined target cells by a retrovirus vector, and to engraftment procedures utilizing the transduced cells.

Another preferred embodiment of the invention provides a method for localizing an amount of a virus, comprising incubating a medium containing the virus in the presence of an effective immobilized amount of fibronectin or fragments of fibronectin containing the viral-binding activity of the Heparin-II binding domain of fibronectin to localize an amount of the virus.

Still other preferred embodiments of the invention generally provide transduced viable hematopoietic and other cellular cultures containing substantially pure and/or immobilized fibronectin or fragments thereof, as well as kits for conducting retroviral-mediated DNA transfer into cells, as further described in the passages which follow.

A still further preferred embodiment of the invention provides a method for obtaining a transduced population of viable cells by a retrovirus, comprising infecting the cells with a retrovirus in the presence of an effective immobilized amount of material such as polypeptide, which amount of immobilized material includes a ligand which binds to the cells and a ligand which which binds the retrovirus, so as to co-localize the retrovirus and the cells and increase the transduction efficiency of the cells. It has further surprisingly been discovered that such processes are more advantageously conducted in the absence or at least the substantial absence of hexadimethrine bromide (also identified as 1,5-dimethyl-1,5-diazaundecamethylene polymethobromide), which heretofore has been used in gene transfer protocols for the desire to increase transduction efficiency. However, surprisingly, the presence of hexadimethrine bromide has been discovered to reduce, rather than increase, transduction efficiency in the co-localization mediated gene transfer processes of the invention. Thus, more preferred processes of the invention are conducted in the absence of hexadimethrine bromide or other agents which increase transduction efficiency in similar protocols conducted in the absence of the material for co-localization, for example in corresponding co-culture protocols. Resultant improved cellular populations and cellular grafting methods also form a part of the present invention.

It is an object of this invention to provide methods for efficient retroviral infection of mammalian cells.

It is a further object of this invention to provide methods for gene transfer with retroviral vectors which avoid the need for cocultivation.

It is a further object of the invention to provide improved methods and cellular cultures for autologous and/or allogeneic cellular grafting.

These and other objects, advantages, and features of the invention will be readily apparent to the skilled artisan from the following description.

DESCRIPTION OF THE FIGURES

FIG. 9 demonstrates that heparin blocks retrovirus binding to fibronectin fragments, as described in Example 9, infra.

FIGS.'s 11 and 12 compare the presence of hADA in mice engrafted with bone marrow cells transduced by (i) the coculture method, (ii) supernatant infection on various fibronectin fragments, and (iii) supernatant infection on BSA, as described in Example 11, infra.

Figure 13:
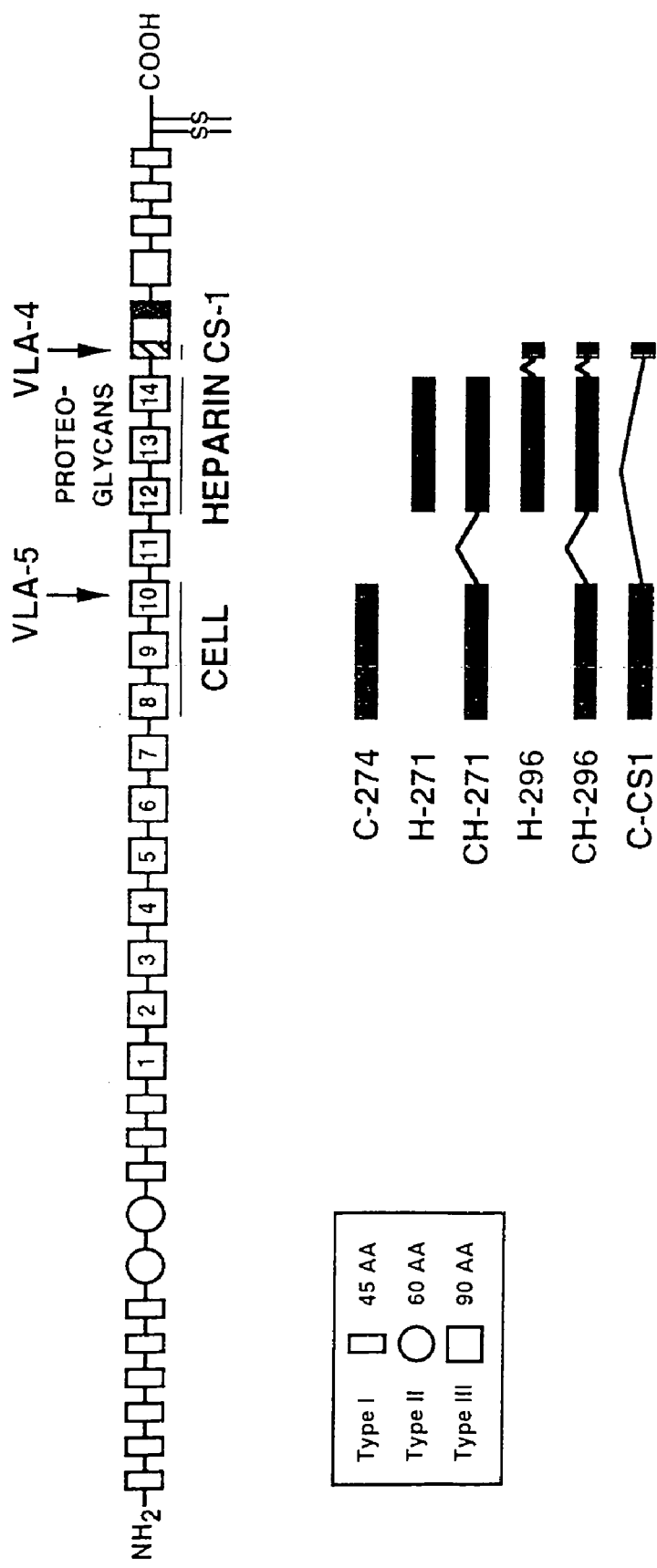

FIG. 13 shows the structure of the α-chain of fibronectin and its relation to the recombinant fragments used in the Examples. The fibronectin type I, II and III repeats are indicated and the type III repeats numbered from 1 to 14. The three binding sites for cells are marked as CELL for cell binding domain (CBD), HEPARIN for heparin binding domain (HBD), and CS1 for the VLA-4 binding site CS1 formed by the first 25 amino acids of the alternatively spliced IIICS region.

Figure 14:
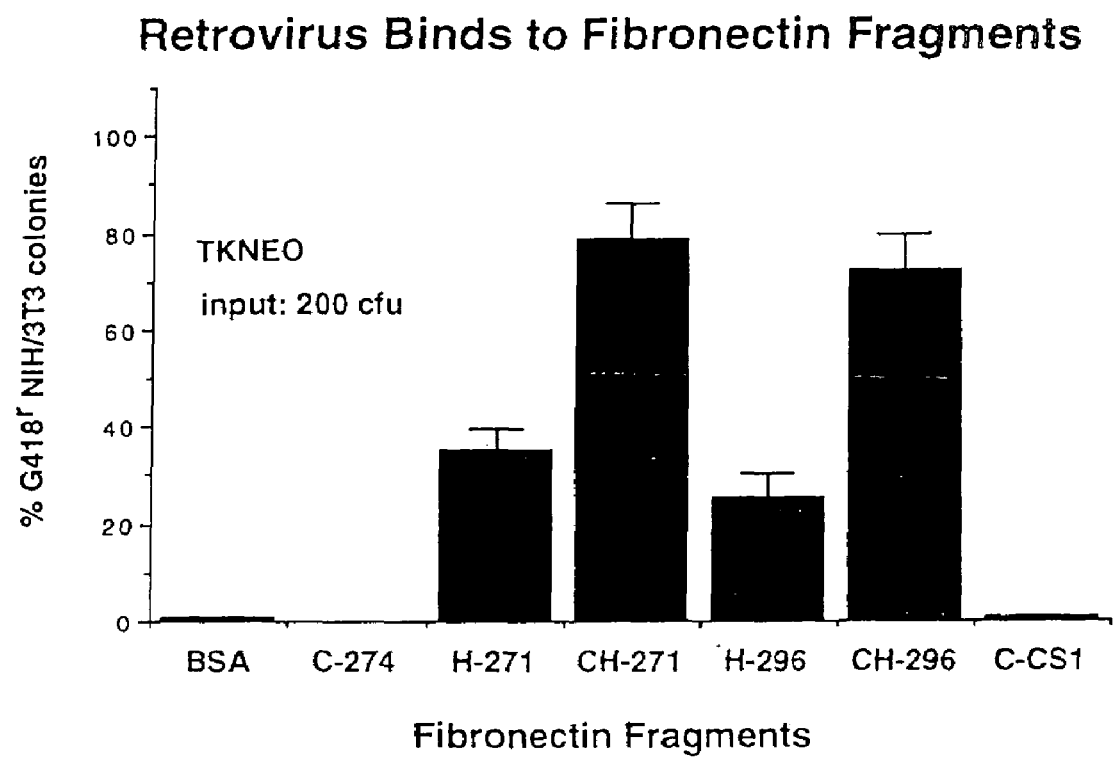

FIG. 14 shows the efficiency of retrovirus infection of NIH/3T3 cells in the presence of various fibronectin fragments, as further reported in Example 12, infra.

Figure 15:
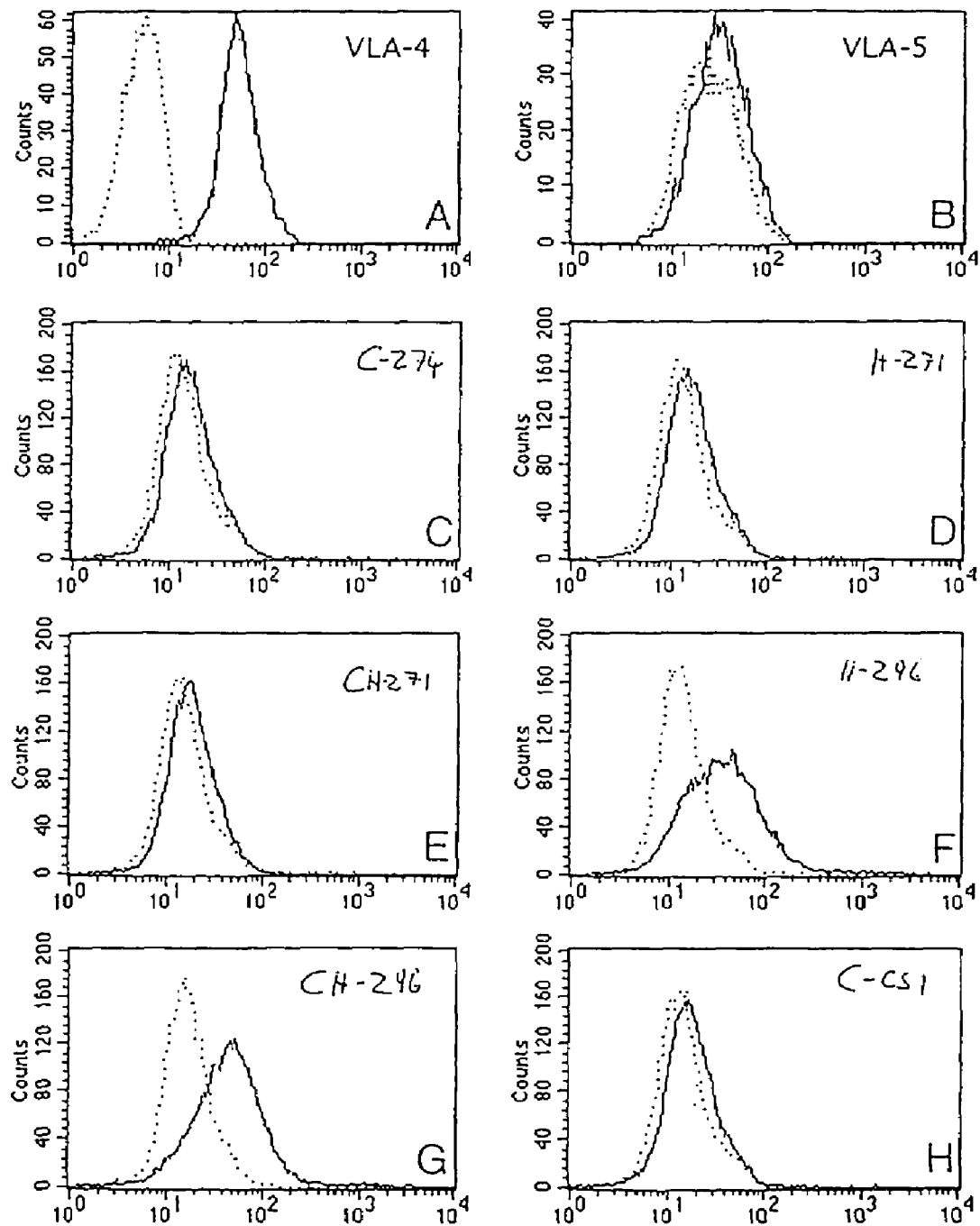

FIG. 15 shows the efficiency of retrovirus infection of non-adherent HL60 cells in the presence of various fibronectin fragments, as further reported in Example 12, infra.

Figure 16:
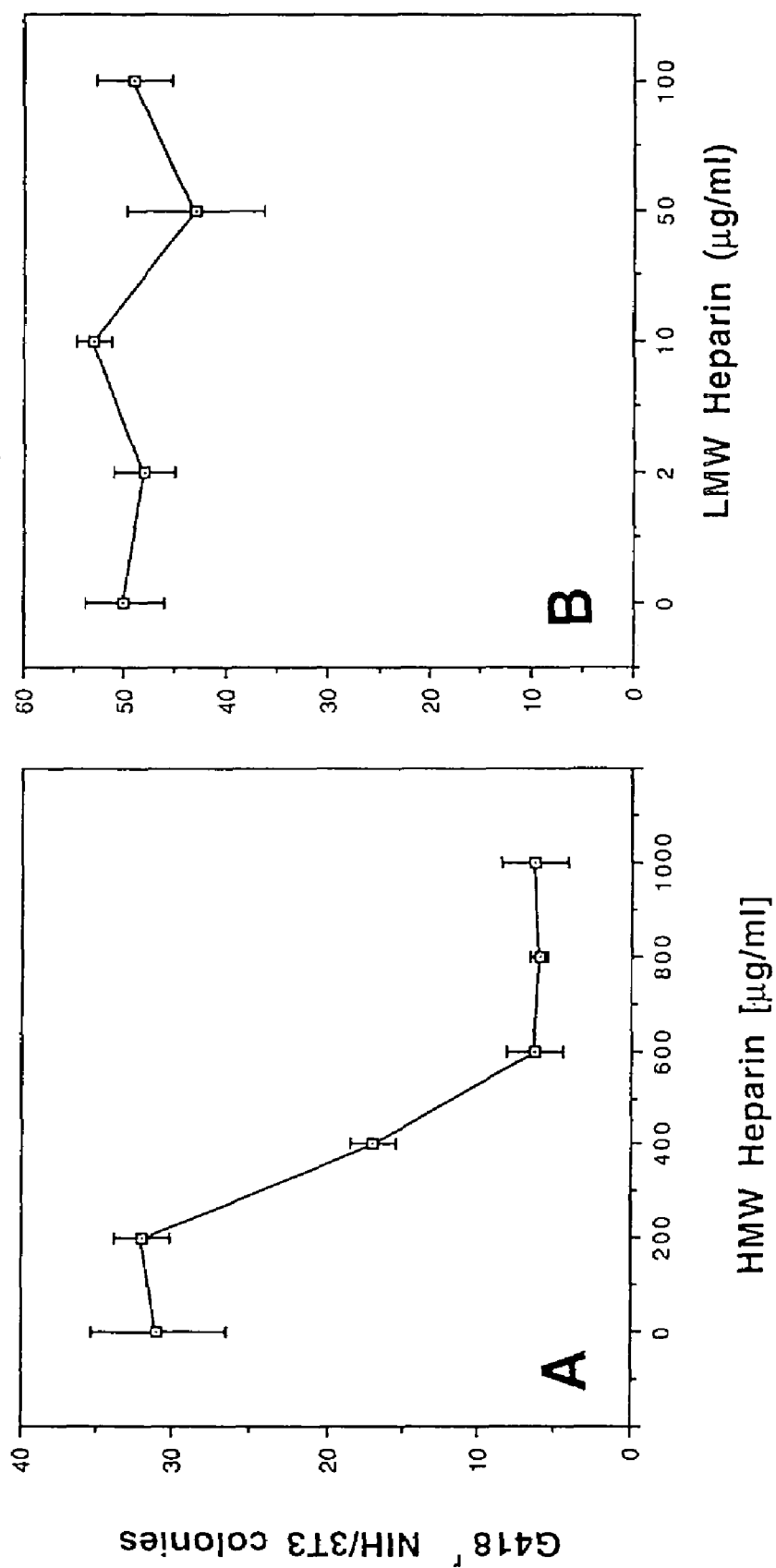

FIG. 16 shows the influence of low and high molecular weight heparin on retrovirus binding to fibronectin.

Figure 17:
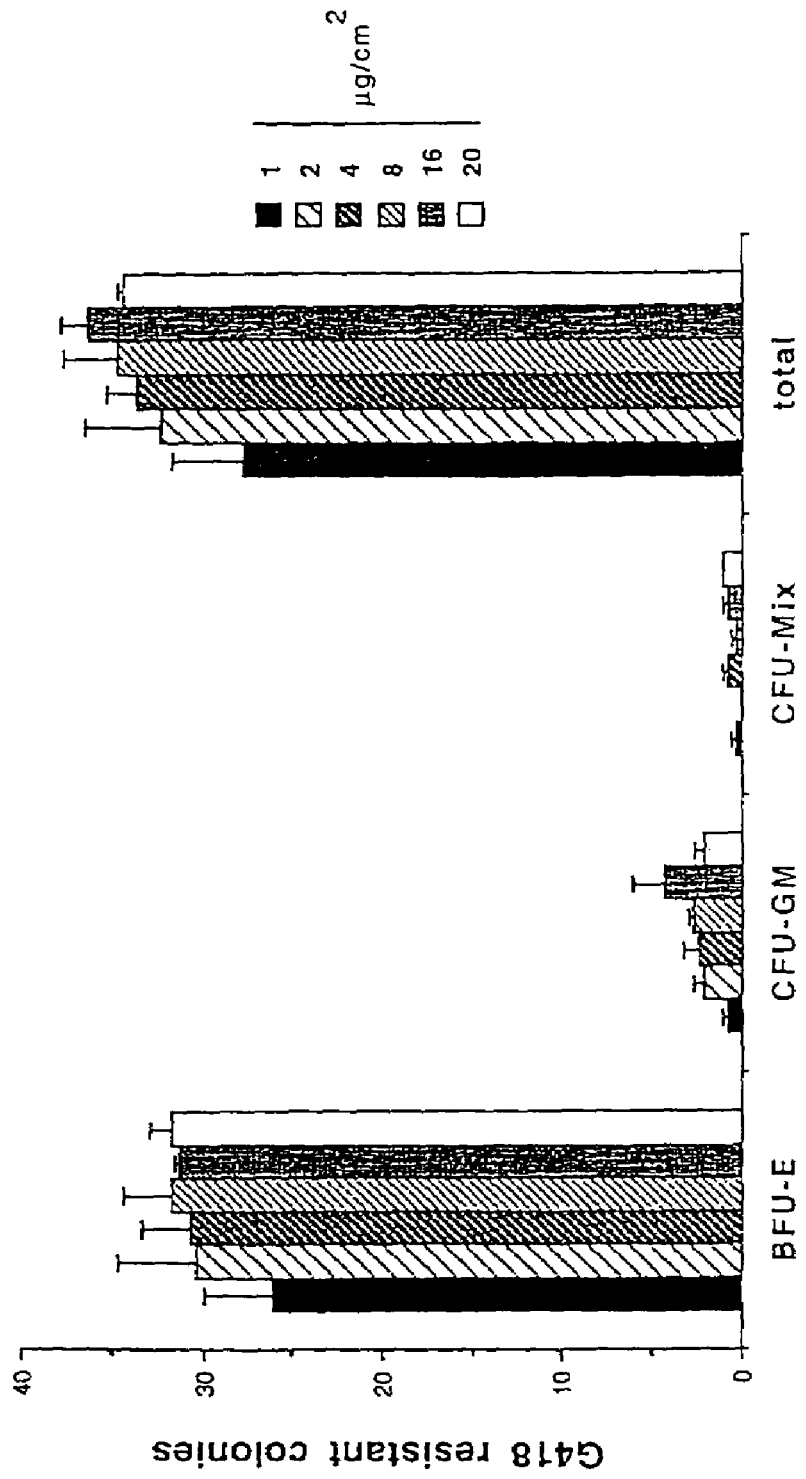

FIG. 17 shows the efficiency of retrovirus infection of various types of progenitor cells within a CD34+ cellular population in the presence of a recombinant fibronectin fragment, as discussed in Example 13, infra.

Figure 18:
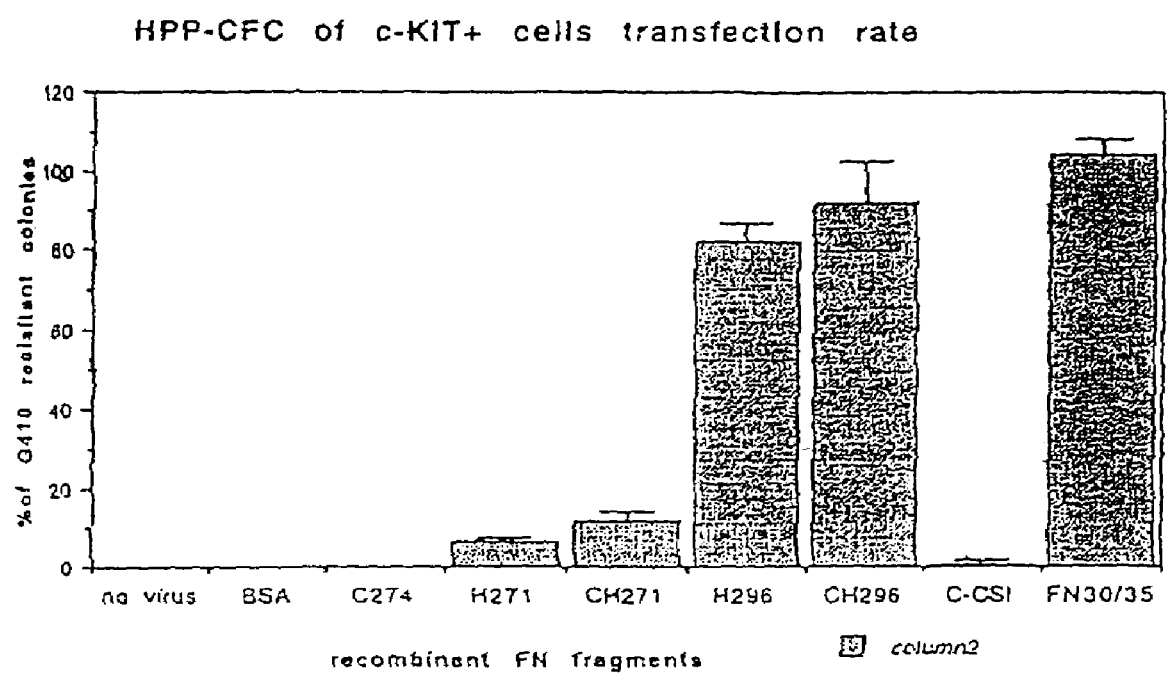

FIG. 18 shows the efficiency of retrovirus infection of HPP-CFC cells in a c-KIT+ cellular population in the presence of a recombinant fibronectin fragment, as discussed in Example 14, infra.

Figure 19:
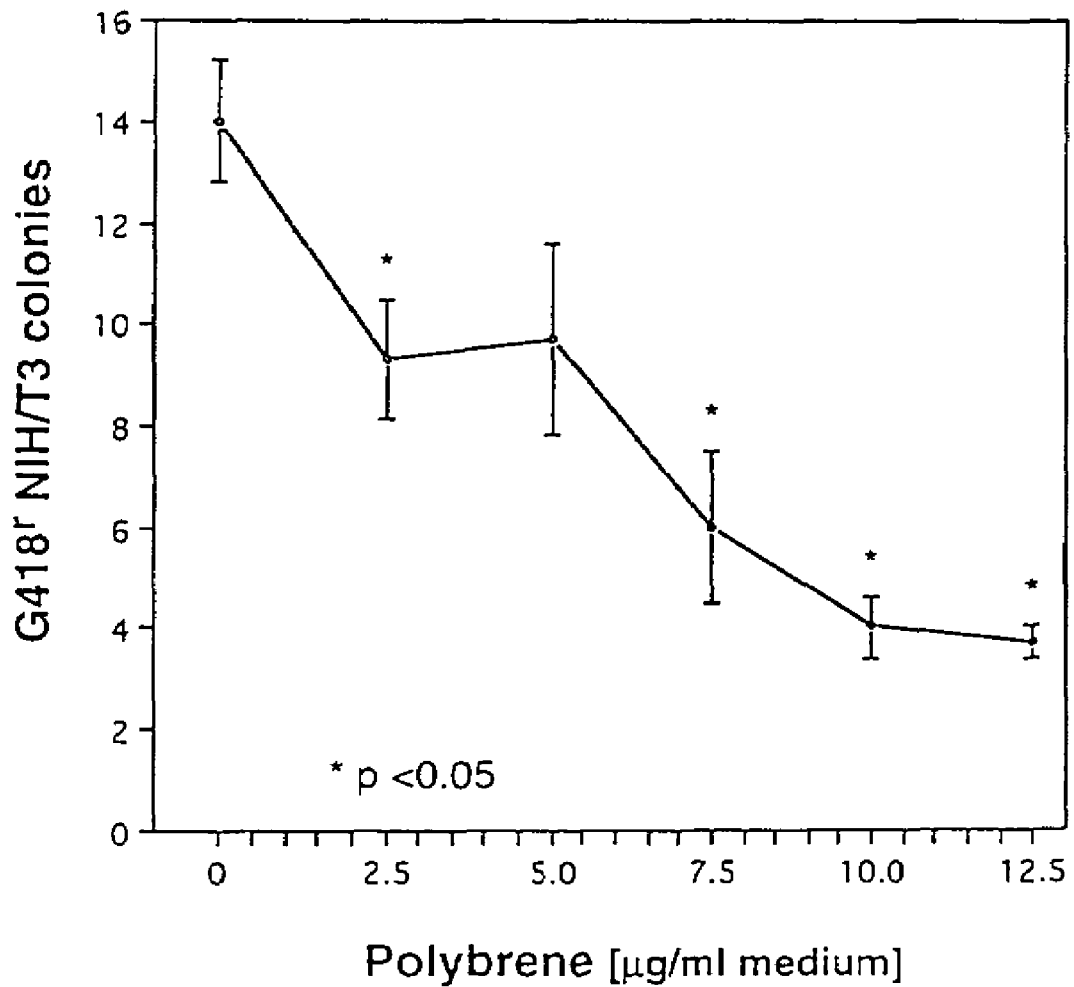

FIG. 19 demonstrates that the efficiency of retroviral infection of NIH/3T3 cells decreases with increasing concentrations of hexadimethrine bromide, as discussed in Example 15, infra.

Figure 20:
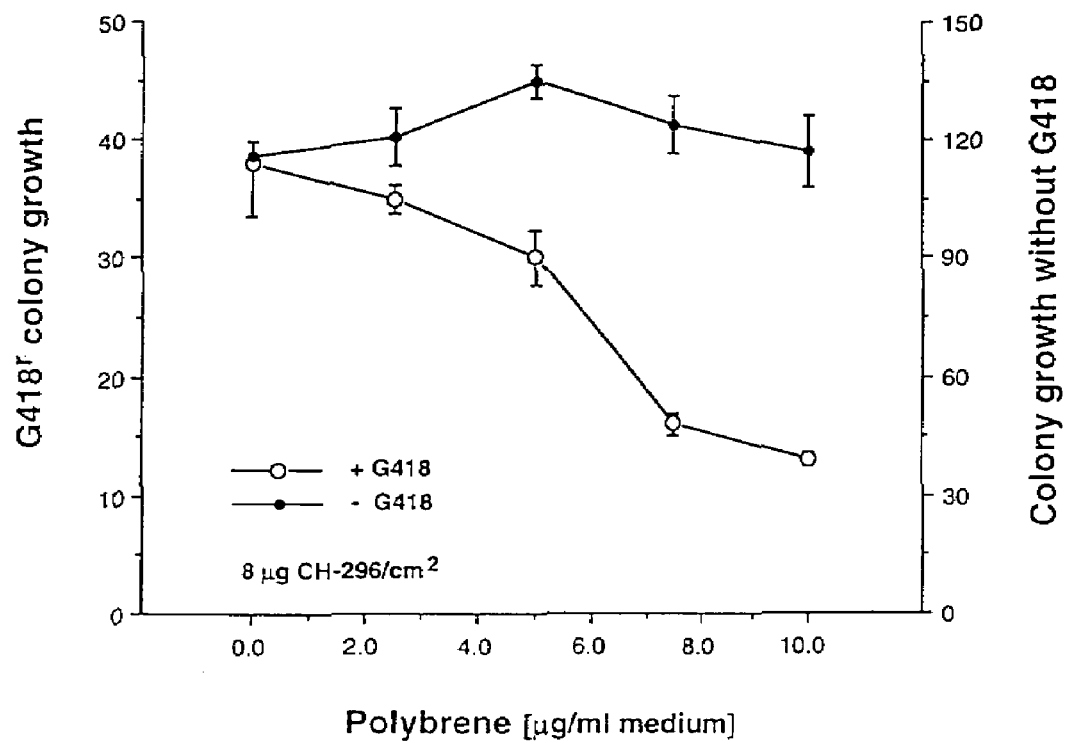

FIG. 20 demonstrates that the efficiency of retroviral infection of clonogenic bone marrow cells decreases with increasing concentrations of hexadimethrine bromide, as discussed in Example 15, infra.

DESCRIPTION OF THE PREFERRED EMBODIMENTS

For the purpose of promoting an understanding of the principles of the invention, reference will now be made to certain embodiments thereof and specific language will be used to describe the same. It will nevertheless be understood that no limitation of the scope of the invention is thereby intended, such alterations, further modifications and such applications of the principles of the invention as illustrated herein being contemplated as would normally occur to one skilled in the art to which the invention relates.

As indicated above, the present invention provides methods for increasing the frequency of transduction of viable cells by viruses such as retroviruses. The invention also provides methods for efficient gene transfer into viable cells using recombinant retroviral vectors, methods for obtaining transduced cells, and methods and materials for achieving autologous and other cellular grafts.

One feature of the present invention is the discovery that fibronectin (FN), and fragments of fibronectin containing the CS-1 cell-adhesion domain of FN, significantly enhance retroviral-mediated gene transfer into cells such as hematopoietic cells, e.g. committed progenitors and primitive hematopoietic stem cells or long-term culture-initiating cells (LTC-IC), carrying a fibronectin receptor and thereby exhibiting the capacity to bind to fibronectin or fragments thereof. Advantageously, this increased efficiency makes cocultivation with virus-producing cells unnecessary. Other features of the invention capitalize on the discovery of a viral-binding domain of fibronectin located within the Heparin-II binding domain. This viral-binding domain can be used to localize virus particles in many applications, including for example in a broad range of constructs for delivering the virus to a target cell.

Recombinant viral vectors in accordance with certain preferred aspects of the present invention contain exogenous DNA and are non-pathogenic, i.e. replication-defective. These vectors efficiently transfer and precisely and stably integrate exogenous DNA into cellular DNA of host cells such as animal cells, particularly mammalian cells. For example, in the present invention a nucleotide sequence including a run of bases from the coding sequence of the gene of interest can be incorporated into a recombinant retroviral vector under the control of a suitable promoter to drive the gene, typically an exogenous promoter. In this regard, the exogenous DNA can contain DNA which has either been naturally or artificially produced, and can be from parts derived from heterologous sources, which parts may be naturally occurring or chemically synthesized molecules, and wherein those parts have been joined by ligation or other means known to the art.

The exogenous DNA incorporated in the virus can be any DNA of interest for introduction into the cells. For example, the exogenous DNA can code for a protein such as ADA which is associated with a known disorder, or an antisense RNA, ribozyme or false primer (See, e.g. WO 90/13641 published Nov. 15, 1990), for an intracellular antibody (See, e.g. WO 94/02610 published Feb. 3, 1994), for a growth factor, or the like.

As indicated, the introduced nucleotide sequence will be under control of a promoter and thus will be generally downstream from the promoter. Stated alternatively, the promoter sequence will be generally upstream (i.e., at the 5' end) of the coding sequence. In this vein, it is well known that there may or may not be other regulatory elements (e.g., enhancer sequences) which cooperate with the promoter and a transcriptional start codon to achieve transcription of the exogenous coding sequence. The phrase "under control of" contemplates the presence of such other elements as are necessary to achieve transcription of the introduced gene. Also, the recombinant DNA will preferably include a termination sequence downstream from the introduced coding sequence.

Retroviral vectors that include exogenous DNA providing a selectable marker or other selectable advantage can be used. For example, the vectors can contain one or more exogenous genes that provide resistance to various selection agents including antibiotics such as neomycin. Representative vectors which can be used in the invention include for example the $N_2$/ZipTKNEO vector (TKNEO) (titer: $1 \times 10^5$ G418$^r$ cfu/ml on NIH 3T3 cells), the ZipPGK-hADA vector, and the ZipPGK-mADA vector all as previously reported by Moritz et al. (1993) *J. Exp. Med.* 178:529. In the TKNEO vector, neo phosphotransferase sequences are expressed in the sense orientation (relative to the 5' long terminal repeat-LTR) via the herpes simplex thymidine kinase promoter. This vector contains a selectable marker gene which provides neomycin resistance to facilitate the identification of transduced cells. In the ZipPGK-hADA vector, the human ADA ("hADA") cDNA is expressed in the sense orientation relative to the 5'LTR via the human phosphoglycerate kinase (PGK) promoter. It contains only one expressible genetic sequence and lacks a dominant selectable marker. The ZipPGK-mADA (PGK-mADA) vector is identical to the ZipPGK-hADA vector except the human ADA cDNA has been replaced with murine ADA ("mADA") DNA. These and other viral vectors and techniques for their production are well known and their implementation and use in the present invention will be well within the skills of those practiced in the art given the disclosure herein.

Viral vectors used in the invention exhibit the capacity to bind to an amino acid sequence of the Heparin-II binding domain of fibronectin, including that of human fibronectin. As discussed in the passages which follow, although the present invention is not limited by any theory, it is believed that co-localization of the virus and the target cell via binding of the virus and cell to respective functional domains facilitates an enhancement in the transduction of the cell by the virus. In this regard, the capacity of a virus to bind to the amino acid sequence of the Heparin-II binding domain and thus to serve effectively in the invention can be readily ascertained using routine procedures such as those described in Examples 8 and 9 below. Generally speaking, these assays determine the extent to which virus particles are bound to immobilized polypeptides containing the Heparin-II binding domain, so as to resist washing from the immobilized polypeptide matrix. Briefly, for instance, a virus-containing supernatant can be incubated in a well containing immobilized polypeptide including the fibronectin Heparin-II binding domain. The well is then extensively washed with physiologic saline buffer, after which target cells to the virus are incubated in the well to determine the level of infectious activity remaining in the well. The reduction in infectious activity, or titer, relative to the initial viral supernatant is assessed and compared to that of a similar control run (e.g. using a BSA-coated well). A significantly higher titer remaining in the Heparin-II domain containing well as compared to the control well signifies that the subject virus is suitable for use in aspects of the invention. To facilitate this screening procedure, the viral vector may contain a selectable marker gene, as discussed above.

Fragments of fibronectin for use in the invention can be of natural or synthetic origin, and can be prepared in substantial purity from naturally-occurring materials, for example as previously described by Ruoslahti et al. (1981) *J. Biol. Chem.* 256: 7277; Patel and Lodish (1986) *J. Cell. Biol.* 102:449; and Bernardi et al. (1987) *J. Cell. Biol.* 105:489. In this regard, reference herein to a substantially pure fibronectin or fibronectin fragments is intended to mean that they are essentially free from other proteins with which fibronectin naturally occurs. Substantially pure fibronectin or fibronectin fragments for use in the invention can also be recombinantly produced, for instance as generally described in U.S. Pat. No. 5,198,423 issued Mar. 30, 1993 to Taguchi et al. and assigned to Takara Shuzo Co., Ltd., Kyoto, Japan. In particular, the recombinant fragments identified in the Examples below as H-271, H-296, CH-271, CH-296 and C-CS1, and methods for obtaining them, are described in detail in this '423 patent. The C274 fragment utilized in the Examples below was obtained as described in U.S. Pat. No. 5,102,988. These fragments or fragments from which they can be routinely derived are available by culturing *E. coli* deposited at the Fermentation Research Institute of the Agency of Industrial Science and Technology, Japan as FERM P-10721 (H-296), FERM BP-2799 (C-277 bound to H-271 via methionine), FERM BP-2800 (C-277 bound to H-296 via methionine), and FERM BP-2264 (H-271), as also described in U.S. Pat. No. 5,198,423. In addition, useful information as to fibronectin fragments utilizable herein or as to starting materials for such fragments may be found in Kimizuka et al., *J. Biochem.* 110, 284–291 (1991), which reports further as to the above-noted recombinant fragments; in *EMBO J.*, 4, 1755–1759 (1985), which reports the structure of the human fibronectin gene; and in *Biochemistry*, 25, 4936–4941 (1986), which reports on the Heparin-II binding domain of human fibronectin. Fibronectin fragments which contain both the CS-1 cell adhesion domain and the Heparin-II binding domain, for example as included in about a 30 or 35 kd fragment (30/35 FN) and in various recombinant fragments as reported in the Examples below, have been found to significantly enhance the efficiency of gene transfer into hematopoietic cells in work thus far, and are preferred for use in the invention. It will thus be understood that, broadly speaking, the fibronectin-related polypeptide or polypeptides utilized in the invention will provide an amino acid sequence providing the cell-binding activity of the CS-1 cell adhesion domain of fibronectin as well as an amino acid sequence of the Heparin-II binding domain of fibronectin which binds the virus. The skilled artisan will recognize that the necessary cell- and virus-binding activities can be provided both by the native amino acid sequences of these functional fibronectin domains and by amino acid sequences which differ from the native sequences yet are sufficiently similar to exhibit the cell-binding and viral-binding activities. These similar amino acid sequences will exhibit substantial sequence homology to their corresponding native sequences, and can include those in which amino acids have been deleted, substituted for and/or modified while nonetheless providing an amino acid sequence with the desired cell-binding or viral-binding characteristic.

In this regard, the pertinent biotechnological arts have advanced to a state in which the deletion, substitution, addition or other modification of amino acids in the subject functional domains can be routinely performed. The resulting amino acid sequences can then be routinely screened for the desired cell-binding or viral-binding activity. For example, viral-binding activity of mutant or modified forms of the Heparin-II-binding domain of fibronectin can be screened as generally discussed above and more specifically below in Examples 8 and 9, using virus incubation, wash, and viral titer assays to determine the retention of infectiousness compared to a control. Given the teachings provided herein, these binding assays will represent but routine experimentation to those working in this field.

Cell-binding to modified or mutant forms of the CS-1 cell adhesion domain of fibronectin, or to other cell-binding polypeptides, can likewise be assayed using conventional procedures. For example, such procedures include those described in *Nature* 352: 438–441 (1991). Briefly, the cell-binding polypeptide is coated on plastic dishes and the cell population to be assayed is overlayed in medium for 30 minutes to 2 hours. After this incubation period, cells non-adherent to the protein are retrieved, counted and assayed for viability. Cells adherent to the polypeptide are also retrieved using trypsin or cell dissociation buffer (e.g. Gibco), counted and viability tested. In some cases, for example for hematopoietic colony forming cells, the cells are further cultured for an additional 12–14 days to ascertain the colony forming characteristics of the cells. The percentage of adherent cells is then calculated and compared to standard to a standard control such as bovine serum albumin (BSA) coated plastic dishes. Substantial binding of the target cells to the assayed polypeptide provides an indication that the polypeptide/cell combination is suitable for the invention, and the polypeptide can be coupled to the retroviral binding fragment from fibronectin to produce a construct of the invention for enhancing the infection of the target cells by the viral vector.

Pursuant to more specific aspects of the invention, the viral-binding polypeptide utilized to enhance transduction by retroviral vectors will comprise (i) a first amino acid sequence which corresponds to the $Ala^{1690}$-$Thr^{1960}$ of the Heparin-II binding domain of human fibronectin, which is represented by the formula (Seq. I.D. #1):

```
Ala Ile Pro Ala Pro Thr Asp Leu Lys Phe Thr Gln Val Thr Pro Thr Ser Leu Ser Ala Gln Trp

Thr Pro Pro Asn Val Gln Leu Thr Gly Tyr Arg Val Arg Val Thr Pro Lys Glu Lys Thr Gly

Pro Met Lys Glu Ile Asn Leu Ala Pro Asp Ser Ser Ser Val Val Val Ser Gly Leu Met Val

Ala Thr Lys Tyr Glu Val Ser Val Tyr Ala Leu Lys Asp Thr Leu Thr Ser Arg Pro Ala Gln

Gly Val Val Thr Thr Leu Glu Asn Val Ser Pro Pro Arg Arg Ala Arg Val Thr Asp Ala Thr

Glu Thr Thr Ile Thr Ile Ser Trp Arg Thr Lys Thr Glu Thr Ile Thr Gly Phe Gln Val Asp Ala

Val Pro Ala Asn Gly Gln Thr Pro Ile Gln Arg Thr Ile Sys Pro Asp Val Arg Ser Tyr Thr Ile

Thr Gly Leu Gln Pro Gly Thr Asp Tyr Lys Ile Tyr Leu Tyr Thr Leu Asn Asp Asn Ala Arg

Ser Ser Pro Val Val Ile Asp Ala Ser Thr Ala Ile Asp Ala Pro Ser Asn Leu Arg Phe Leu Ala

Thr Thr Pro Asn Ser Leu Leu Val Ser Trp Gln Pro Pro Arg Ala Arg Ile Thr Gly Tyr Ile Ile

Lys Tyr Glu Sys Pro Gly Sev Pro Pro Arg Glu Val Val Pro Arg Pro Arg Pro Gly Val Thr

Glu Ala Thr Ile Thr Gly Leu Glu Pro Gly Thr Glu Tyr Thr Ile Tyr Val Ile Ala Leu Lys Asn

Asn Gln Lys Ser Glu Pro Leu Ile Gly Arg Lys Lys Thr;
``` or a sufficiently similar amino acid sequence thereto to exhibit the ability to bind the retrovirus;

and (ii) a second amino acid sequence which corresponds to one portion of the IIICS binding domain of human fibronectin (the CS-1 cell binding domain); which is represented by the formula (Seq. I.D. #2):

```
Asp Glu Leu Pro Gln Leu Val Thr Leu Pro His Pro Asn Leu His Gly Pro Glu Ile Leu

Asp Val Pro Ser Thr;
``` or a sufficiently similar amino acid sequence thereto to exhibit the ability to bind hematopoietic cells such as primitive progenitor and/or long term repopulating (stem) cells.

As mentioned previously, it will be understood that certain modifications and/or mutations of these native sequences are possible within the practice of the present invention, so long as the resulting amino acid sequence is sufficiently similar to the native sequence to exhibit the ability to bind the virus (in the case of the Heparin-II-binding domain) and the ability to bind the target cells (in the case of the CS-1 domain).

One aspect of the invention provides a method of somatic gene therapy which involves in vitro cellular therapy and subsequent transplantation of target cells into a host, also known as "engraftment" of the host with the transduced target cells. Hematopoietic or other cells, for instance stem cells isolated from bone marrow or peripheral blood, embyronic stem cells, or cells otherwise characterized as CD34+ and/or C-kit+, can be collected from a human or other mammalian animal source using standard protocols. For example, the hematopoietic cells can be collected from bone marrow or peripheral blood of a human donor or from human fetal umbilical cord blood. Once collected, the hematopoietic cells can optionally be treated by standard techniques to enrich them in stem cells and/or primitive progenitor cells. The hematopoietic cells can then be suitably incubated, for instance on tissue culture plates. Optionally during this period, adherent-negative low density mononuclear cells can be prestimulated prior to retroviral infection. Prestimulation as known in the art and as used herein refers to the process of exposing cells to growth stimulating factors before exposure to retroviruses. Such prestimulation has proven to improve the transduction of hematopoietic cells by retroviruses.

Subsequent to prestimulation, the cells can be harvested and incubated with fibronectin or fragments thereof as described herein which enhance the frequency of cellular transduction by retroviruses. Preferably, the cells are incubated with purified and/or insoluble, e.g., immobilized fibronectin or fibronectin fragments. The cells can then be infected with the recombinant virus, for instance a retrovirus containing a gene for correcting an enzyme or other protein deficiency or abnormality in the cells, in the presence of an amount of the fibronectin or fibronectin fragment effective to increase the frequency of transduction of the cells by the virus. The resulting transduced hematopoietic cells can then be conventionally introduced, e.g. intravenously, into an animal cellular graft recipient, preferably an autologous donor but also including allogeneic transplants, the latter especially where umbilical cord blood cells are used for the graft as discussed below.

Methods of the invention can be used in gene marking or gene therapy protocols for a variety of disorders including bone marrow disorders, including for example cancers, leukemias, disorders involving protein deficiencies or abnormalities, and therapies for modifying hematopoietic cells to improve resistance to other therapeutic protocols such as chemotherapy. Representative disorders with which the invention may be used thus include ADA deficiency, e.g. ADA-deficient SCID, pediatric acute myelogenous leukemia (AML), neuroblastoma, and adult AML and acute lymphocytic leukemia (ALL).

In one particularly preferred embodiment of the invention, the cells utilized for a cellular graft are obtained from human umbilical cord blood. Thus, human umbilical cord blood can be collected and enriched in viable primitive hematopoietic progenitor and/or stem cells, for example by obtaining an adherent-negative, low density, mononuclear cell population. This population is then optionally prestimulated, and incubated in the presence of a retroviral vector and immobilized and/or purified fibronectin or fibronectin fragments, to enhance the transduction efficiency of the cells by the vector. In this regard it has been found that the transduction of the primitive hematopoietic and/or stem cells from umbilical cord blood is greatly enhanced in the presence of the fibronectin or fibronectin fragments, even though fibronectin does not constitute part of the ECM in cord blood and even though primitive progenitor and stem cells from cord blood have been characterized as different from those from bone marrow. In particular, the cord blood stem cell has been characterized as $CD34^+$, $HLA-DR^+$, whereas the stem cell from bone marrow has been characterized as $CD34^+$, $HLA-DR^-$. The discovery that primitive progenitor cells from umbilical cord blood are effectively transduced in an enhanced fashion in the presence of the fibronectin or fibronectin fragments enables the use of a convenient and highly stem-cell-enriched source of hematopoietic cells. Moreover, evidence of successful engraftment of numerous patients with allogeneic transplants of cord blood enriched for primitive progenitor and stem cells, makes cord blood a highly preferred source for hematopoietic cells. See, Kohli-Kummer et al., *Brit. Heaematol.* 85:419–422 (1993); Broxmeyer et al., *Blood Cell* 17:313–329 (1991); Gluckman et al., *Br. J. Heaematol.* 45:557 (1980); Heidelberg: Springer-Verlag pp. 60–68 (1989); Wagner et al., *Blood* 79:1874–1881 (1992); and Wagner et al., *Blood* 82–86a (Abstract).

If desired, harvested transduced hematopoietic or other cells can be tested for transduction efficiency and gene expression. For instance, the significant improvements in retrovirus-mediated gene transfer provided by the invention are demonstrated in the specific Examples below, which describe several tests demonstrating high infection and gene transfer efficiency by retroviruses in the presence of fibronectin or effective fibronectin fragments. In particular, murine hematopoietic cells infected with PGK-hADA retrovirus expressed high levels of the transferred ADA cDNA. Similarly, individual PGK-mADA virus infected human progenitor colonies expressed murine ADA levels up to 10-fold higher than the endogenous human ADA protein. Therefore, to stringently analyze transfer efficiency, progenitor colonies were considered transduced only if expression of the transferred mADA was equal to or greater than endogenous human ADA levels. High levels of expression of neo from the TKNEO vector were detected by G418 drug resistance, as an assay for neophosphotransferase (the neo gene product) activity.

As indicated above, methods of the present invention are advantageously conducted without the need for cocultivation in the presence of retroviral producer cells. Thus, in accordance with one aspect of the invention, the retroviral-mediated gene transfer can be carried out in the substantial absence of cells other than the target hematopoietic or other cells. For example, producer cells containing the retroviral vector plasmid can be cultured and supernatant collected. The retroviral-containing supernatant can then be utilized to infect the hematopoietic cells in the presence of the fibronectin and/or fibronectin fragments, which are preferably in immobilized form, e.g. coated on a substrate upon which the infection is carried out or otherwise in contact with the medium for infection. In this regard, any producer cells which produce high-titer helper-free retroviruses are contemplated as suitable for use in the invention. These include, for example, packaging cells such as Psi-2, C2, PA12, PA317, and GP+envAM12, as well as many other packaging cell lines known in the art.

In accordance with other features of the invention, the strong virus binding to amino acids within the Heparin-II binding domain of fibronectin may be used for constructing delivery systems for viral therapy across a broad range of cell types. To this end, a polypeptide including the retrovirus binding domain from fibronectin may be covalently coupled to any ligand which gives this construct specificity for the target cells. This approach will circumvent the prior necessity of constructing specific retrovirus cell lines for each target cell (Kasahara, N., A. M. Dozy, and Y. W. Kan., *Science* Vol. 266, pp. 1373–1376 (1994) and Valsesia-Wittmann, S., A. Drynda, G. Deleage, M. Aumailley, J. M. Heard, O. Danos, G. Verdier, and F. L. Cosset, *J. Virol.*, Vol. 68, pp 4609–4619 (1994)). The specificity of the targeting construct may be provided by employing ligands including for example 1) cell adhesive protein, 2) hormones or cytokines, 3) monoclonal antibodies to the target cells, 4) carbohydrates which bind the target cells (G. Ashwell, et al., *Annu. Rev. Biochem.*, Vol. 51, pp. 531–554 (1982)), 5) metabolites for the target cells, or 6) functional polypeptides which bind the target cells. The efficiency of the construct for gene delivery may be improved by including several Heparin-II virus binding domains and therefore increasing the amount of viral particles delivered to the target cells. For example, the cell-binding domain of human fibronectin which corresponds to $Pro^{1239}$-$Ser^{1515}$, as described in U.S. Pat. No. 5,198,423, has been shown to bind to cells including BHK and B16-F10 cells (Kimizuka et al., *J. Biochem. Vol.* 110, pp. 285–291 (1991)). In addition, the Heparin-II domain itself has been shown to bind to fibroblasts, endothelial cells, and tumor cells. These polypeptide sequences may be coupled to the retrovirus binding domain from fibronectin to target predetermined cells for infection by retrovirus.

Exemplary applications in the hematopoietic system also include a construct of erythropoietin or G-CSF coupled to the retrovirus binding domain of fibronectin for targeting highly specific erythroid or granulocytic precursor cells, respectively. Another common application in accordance with the present invention will be to combine the retrovirus binding domain or domains with a ligand which specifically or predominantly binds to malignant cells. For example, it has been shown that in vitro and even in vivo growth of breast carcinoma cells can be influenced employing substances binding to receptors on the target cells like luteinizing hormone releasing derivatives, Emons, G. et al., *Hum. Reprod.* 9:1364–1379 (1994), oestrogens, Tolcher, A. W., *Oncol.* 8:39–43 (1994), or anti-oestrogens, Howell, A. et al., *Lancet* 345:29–30 (1995), progestogens or anti-progestogens, Klijn. F. G. et al, *Hum. Reprod.* 9 Suppl. 1:181–189 (1994); Griffiths, K. et al, *Semin. Oncol.* 21:672–687 (1994), which will serve as ligands in constructs of the invention containing one or more virus binding domains from fibronectin. As further examples, thyroid (cancer) cells may be targeted highly specifically by using constructs with Jodid, and liver (cancer) cells may by targeted by constructs containing HDL or parts thereof. Finally, constructs of monoclonal antibodies and the retrovirus-binding domain of fibronectin will allow the targeting of any cell and organ against which an antibody is available. A broad range of mammalian cell types are thus targetable by capitalizing upon the ability of the retrovirus binding domain of fibrobnectin to bind and localize viral vectors.

Accordingly, another preferred embodiment of the invention involves the preparation of construct which can be used to enhance the viral transduction of a target cell. The viral-binding amino acid sequence of the Heparin-II-binding domain of fibronectin is coupled to a ligand to which the target cell binds. As discussed above, the ligand may be, for example, a polypeptide from fibronectin or from another protein (including a cell adhesive protein, for example laminin, collagen, vitronectin, osteopontin or thrombospondin), a hormone, a metabolite, an antibody (including monoclonal antibodies), or any other ligand exhibiting the capacity to bind; preferably with specificity, to the target cell. The resulting overall construct can be used in immobilized form in a fashion similar to that used for the fibronectin polypeptides specifically exemplified in the Examples below.

Such constructs and cell-targeting approaches may be utilized in vitro as discussed above, and also in in vivo targeting of retroviruses, taking into account various factors such as the stability and specificity of the construct and the retrovirus construct interaction under physiological conditions. The specificity may also be improved by modifying the delivery system to localize delivery of the construct to the target cells, for instance catheterizing the portal vein for targeting liver cells.

Another aspect of the invention relates to the discovery that the transduction processes of the invention, which involve co-localization of the virus and the cells; are more advantageous when conducted in the absence or substantial absence of hexadimethrine bromide. Hexadimethrine bromide (commercially available under the name Polybrene®) is a polycationic substance which has been extensively used in retroviral-mediated gene transfer protocols for the purpose of improving the tranduction efficiency by the retrovirus. Nonetheless, it has been discovered that the presence of hexadimethrine bromide in co-localization enhanced gene transfer protocols such as those described herein significantly reduces transduction efficiency. Thus, improved processes of the invention are conducted in a medium at least substantially free from hexadimethrine bromide (i.e. containing no more than about 1 µg/ml hexadimethrine bromide) and more preferably in the absence of hexadimethrine bromide. Such processes provide preferred cellular compositions of the invention, which include substantially retroviral-transduced viable cellular populations which are substantially free from both retroviral producer cells and hexadimethrine bromide. In this regard, substantially transduced viable cellular populations as used herein is intended to mean that at least about 20% of the cells in the population have been tranduced by a retrovirus. More preferred populations will have at least about 50% transduced cells, and most preferably at least about 75% transduced cells. Preferred cellular compositions in accordance with this aspect of the invention will include hematopoietic cells, and more preferably will include hematopoietic cellular populations which are enriched in primative progenitor and stem cells. Generally speaking, advantageous processes of the invention can thus be conducted without the presence of polycationic or other agents which, in corresponding retroviral infection protocols (e.g. co-culture) without the fibronectin fragment or other material for co-localization, lead to an increase in transduction efficiency, but which agents reduce the transduction efficiency in the presence of the material for co-localization.

It is contemplated that highly convenient retroviral-mediated DNA transfer will be carried out utilizing kits specially designed to practice methods of the invention. Accordingly, another aspect of the invention provides kits which include an amount of the substantially pure polypeptide or construct discussed above which enhances the transduction of target cells by retroviruses, along with an artificial substrate upon which the retroviral infection can be carried out. The polypeptide or other construct can be provided separately or coated upon the artificial substrate. In the case of infection protocols for human hematopoietic cells the kits will also include hematopoietic cell growth factors for cell prestimulation. In addition, the kits can include the recombinant retrovirus vectors as discussed above for the transduction. Generally speaking, the kits will include sterile packaging which secures these various kit components in spaced relation from one another sufficient to prevent breakage of the components during handling of the kit. For example, it is a common practice to utilize molded plastic articles having multiple compartments or areas for holding the kit components in spaced relation.

In order to promote a further understanding and appreciation of the invention, the following specific Examples are provided. It will be understood that these examples are illustrative and not limiting in nature.

EXAMPLE 1

Gene Transfer into Bone Marrow Cells Using TKNEO 1.1. Preparation of Virus-Supernatant GP+EnvAM 12 producer cells (see Markowitz et al. (1988) *Virology* 167:400) containing retroviral plasmid TKNEO vector were cultured in Iscove's Modified Dulbeccos Medium (IMDM, Gibco, Gaithersburg, Md.) containing 10% fetal calf serum (FCS, Hyclone, Logan, Utah) and 100 units/ml penicillin and 100 microgram/ml streptomycin (P/S, both Gibco). Virus containing supernatant was collected by adding 10 ml of IMDM containing 20% FCS to confluent plates overnight. Harvested medium was filtered through 0.45 micron filters (Gelman Sciences, Ann Arbor, Mich.) and stored at −80° C. until used.

1.2. Preparation of Fibronectin Fragments

FN was purified from human plasma (Lifesource, Glenview, Ill.) as previously described in Ruoslahti et al., *Methods Enzymol.* 82:803–831 (1982), except that the gelatin-agarose column was washed with 1M urea prior to elution of FN with 4M urea. Purified FN was dialyzed extensively at 4° C. against 10 mM 3-(cyclohexylamino)-1-propane-sulfonic acid (CAPS), 150 mM NaCl, 2 mM $CaCl_2$ pH 11.0 and stored in aliquots at −80° C. The chymotryptic cell binding domain (CBD) (CS-1) and Heparin-II binding fragments of FN were purified as previously described (Ruoslahti et al. (1982), supra, Patel and Lodish, *J. Cell. Biol.* 102, pp. 449–456 (1986), and Bernardi et al., *J. Cell. Biol.* 105, pp. 489–498 (1987). Three major heparin-binding fragments (30kD, 35kD, and 42kD) were obtained in the 1M NaCl eluate from the heparin-agarose column. To further purify these heparin-binding fragments, the 1M NaCl eluate was dialyzed overnight at 4° C. against 10 mM Tris-HCl, pH 7.0 and passed over an anion exchange column (2 ml DEAE sepharose fast flow (Pharmacia Fine Chemicals, Uppsala, Sweden)/mg of protein) that had been equilibrated with 10 mM Tris-HCl pH 7.0. The 30/35kD fragments were collected in the unbound fraction while the 42kD fragment was eluted from the column with 100 mM NaCl. From 500 mg of FN, approximately 26 mg of the 30/35kD fragments and 4 mg of the 42kD fragment were obtained. The 42kD fragment, but not the 30/35kD fragments, were recognized by an antibody against the fibrin-binding domain, as determined by western blotting technique. Also, the 42kD fragment binds to a fibrin-sepharose affinity column.

For use in the infection protocol, fibronectin fragments were immobilized on 35 or 100 mm petri dishes (Falcon, Lincoln Park, N.J.) at a concentration of 75 pmol/cm$^2$ as described by Patel and Lodish (1986), supra. Control plates were coated in analogous fashion with 2% (FN-free) bovine serum albumin (BSA, Boehringer Mannheim, Mannheim, Germany).

1.3. Retroviral Infection Protocol

Bone marrow samples from healthy adult donors were collected in tubes containing sterile, preservative-free sodium sulfate heparin according to protocols approved by the Institutional Review Board of Indiana University School of Medicine. Low density mononuclear cells were prepared by centrifugation on Ficoll-Hypaque (density 1.077 g/ml, Pharmacia, Piscataway, N.J.) for 45 minutes at 25° C. Plastic adherent cells were removed from low density bone marrow cells by an additional incubation on tissue culture plates for 4–16 hours at 37° C. in 5% $CO_2$ in IMDM with 2-% FCS.

Adherent-negative low density mononuclear cells were prestimulated prior to retroviral infection as described previously by Luskey et al. (1992) *Blood* 80:396, for 48 hours at 37° C. and 5% $CO_2$ in IMDM containing 20% FCS, 100 U/ml rhIL-6, 100 ng/ml rhSCF (both Amgen, Thousand Oaks, Calif.), and P/S at a cell density of 1×10$^6$ cells/ml in petri dishes. Prestimulated cells were harvested by vigorously pipetting to remove cells loosely adherent to the plastic.

Prestimulated cells (5×10$^5$ cells/ml) were incubated for 6 hours on plates coated with BSA (control plates) or fibronectin or fragments thereof (subjected to UV radiation to better adhere the proteins to the plastic plate) and then infected with virus supernatant in the presence of growth factors (as above) and 7.5 micrograms/ml polybrene (Aldrich Chemical, Milwaukee, Wis.). Virus supernatant was replaced (including growth factors and 5.0 microgram/ml polybrene) after 2 hours and cells were incubated for an additional 12 to 24 hours. Non-adherent cells were re-added with each media change.

Following the infection protocol, non-adherent cells were decanted and adherent hematopoietic cells were collected from the cultures using Cell Dissociation Buffer (CDB) (enzyme free/PBS based, Gibco) according to the manufacturer's instructions. The adherent cells were added to the non-adherent fraction, washed twice and counted. Harvested cells were either plated in clonogenic methylcellulose progenitor assays or long term bone marrow cultures.

1.4. Long Term Bone Marrow Cultures

LTC-IC (human stem cell) assays were performed according to previously described methods with slight modifications. Sutherland et al. *Blood* 74:1563 (1989). Briefly, 0.5–1×10$^6$ infected cells were seeded in long term bone marrow cultures (LTMC) on confluent, pre-irradiated (as above) allogenic human bone marrow fibroblasts (BMF) in 5 ml IMDM containing 10% FCS, 10% horse serum (Sigma) and p/S, 1×10$^{-5}$ M hydrocortisone (Upjohn, Kalamazoo, Mich.), and 320 mosmol sodium chloride in 6 well tissue culture plates (Costar, Cambridge, Mass.). LTMC were incubated at 33° C. in 5% $CO_2$ and fed weekly by removal of 50% of the media and non-adherent cells. After five weeks, LTC-IC cultures were sacrificed by using CDB to remove adherent hematopoietic cells from BMF. Both non-adherent and adherent hematopoietic cells were combined and plated in methylcellulose to obtain colonies derived from LTC-IC.

1.5. Clonogenic Methylcellulose Assays

Methylcellulose assays were performed as previously described by Toksoz et al. *Proc. Nat. Acad. Sci., USA*, Vol. 89, p 7350 (1992), with minor modifications. Briefly, 2–5×10$^4$ infected adult bone marrow cells were plated with 5 units/ml erythropoietin (Epo, Amgen), 100 ng/ml rhSCF, 10 ng/ml rhIL-3 (Genzyme, Cambridge, Mass.) in 1 ml of 2.4% IMDM methylcellulose (Fluka, Ronkonkoma, N.Y.) containing 25% FCS, 10% human plasma, 10$^{-5}$ M beta-mercaptoethanol (Sigma), and P/S. Cultures were incubated at 37° C. in 5% $CO_2$/95% air and colonies (>50 cells) were scored by viewing on an inverted microscope on day 13 as CFU-GM (containing granulocytes and macrophages), CFU-Mix (containing myeloid and erythroid elements), or BFU-E (containing only erythroid elements).

1.6. Analysis of Retroviral Infection

Efficiency of infection with the TKNEO virus was analyzed by determining the percent of methylcellulose colonies resistant to 1.5 mg/ml (dry powder, Gibco) G418 on day 13. Mock infections were performed in each experiment by incubating bone marrow on the GP+EnvAM 12 packaging line making no recombinant virus. Culture of these mock infected cells with 1.5 mg/ml G418 consistently demonstrated <1% background colonies.

1.7. Gene Transfer Efficiency into Committed Progenitor Cells

Figure 2:
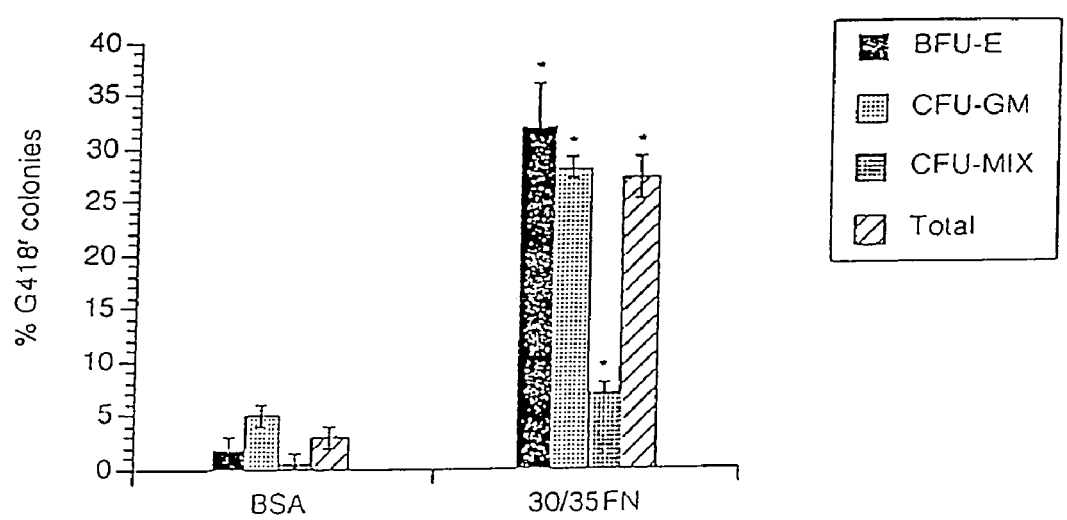
FIG. 2 shows the infection efficiency of committed human progenitor cells in the presence of fibronectin fragments using the TKNEO vector, as further described in Example 1, infra.

Transduction efficiency was compared by infecting bone marrow cells while plated on 30/35 FN- or BSA-coated dishes. No difference in the number of colonies obtained after infection without selection was observed between these conditions. FIG. 2 demonstrates the percentage of G418$^r$ colonies after infection. A higher percentage of G418$^r$ colonies was noted on 30/35 FN from all types of progenitors, including those derived from lineage-restricted (BFU-E and CFU-GM) as well as multilineage (CFU-Mix) progenitor cells. Infection into all committed progenitors was increased 9-fold on 30/35 FN versus BSA.

1.8. Gene Transfer Efficiency into Long Term Culture-Initiating Cells

Gene transfer into LTC-IC was assessed using the TKNEO vector. Gene transfer into LTC-IC derived colonies was only detected after infection on 30/35 FN (16% G418$^r$ vs 0% G418$^r$ colonies, 30/35 FN vs BSA).

Figure 1:
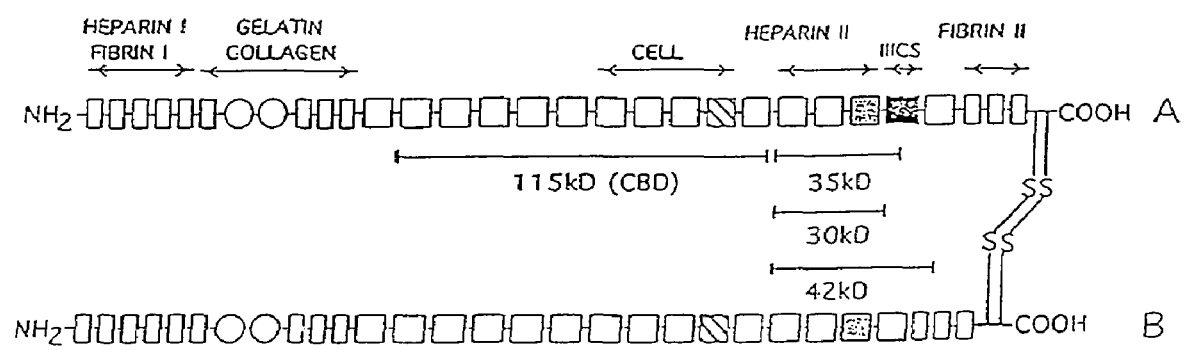
FIG. 1 provides a schematic representation of a fibronectin molecule, including chymotryptic fragments.
Figure 3:
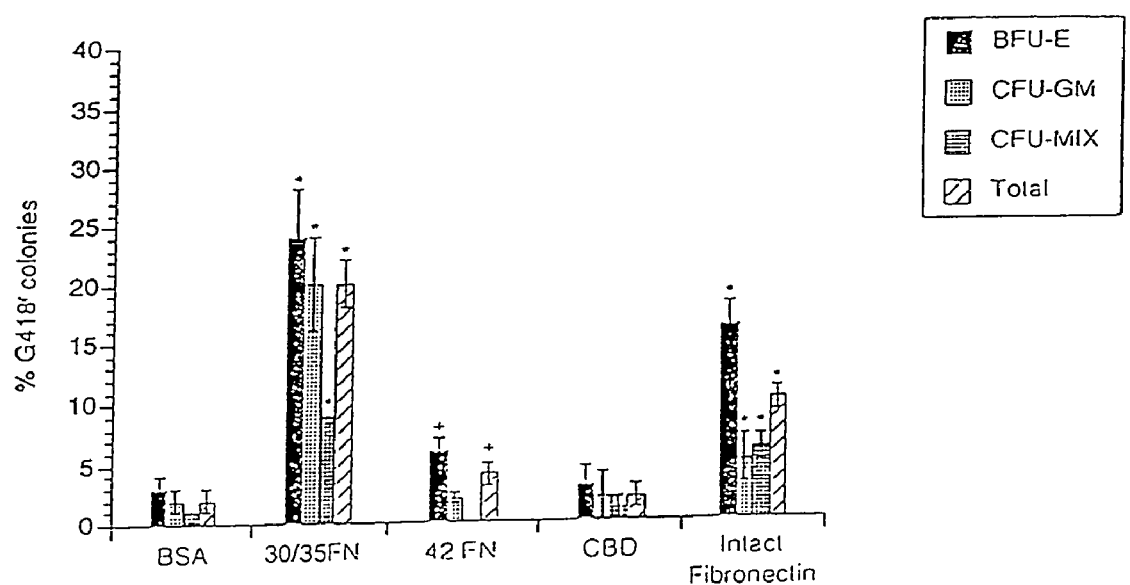
FIG. 3 compares the infection efficiency of various committed human hematopoietic progenitor cells in the presence of fibronectin fragments thereof using the TKNEO vector, as further described in Example 1, infra.

1.9. Specificity of 30/35 FN Effects on Infection Efficiency of Hematopoietic Cells To determine the specificity of increased gene transfer efficiency seen on 30/35 FN, infection with TKNEO was performed on plates coated with BSA, 30/35 FN, intact fibronectin, a 115 kd FN fragment containing the central cell-binding domain (CBD) containing the RGDS tetrapeptide sequence, and a 42 kd C-terminal FN fragment (42FN) characterized by the Heparin-II binding domain but lacking the CS-1 sequence (FIG. 1). Infection on BSA yielded 3±1% G418$^r$ BFU-E, 1±1% G418$^r$ CFU-GM, and 0±0% G418$^r$ CFU-MIX. No significant increase in the proportion of G418$^r$ colonies were noted on CBD, while slightly higher infection of BFU-E (6.0±–1%) were seen on 42 FN (FIG. 3). However, intact FN promoted increased gene transfer into all committed progenitors. The percentage of G418$^r$ colonies after infection on intact FN were less than on 30/35 FN in all lineages, including BFU-E (16±–2 vs. 24±4%), CFU-GM (5±2 vs 20±4%) and CFU-Mix (6±1 vs 9±1; intact FN vs 30/35 FN, respectively.

EXAMPLE 2

Gene Transfer into Bone Marrow Cells Using PGK-mADA 2.1. General Procedures

PGK-mADA virus supernatant was prepared as described for TKNEO in Example 1. Chymotryptic fragments of fibronectin (FIG. 1) were prepared as previously described in Example 1 and the retroviral infection protocol of Example 1 was followed. LTC-IC (human stem cells) assays and Methylcellulose assays were performed according to Example 1.

2.2. Analysis of Retroviral Infection

Efficiency of infection with the PGK-mADA vector was determined by protein analysis using ADA isoenzyme electrophoresis. Analysis of individual progenitor colonies was performed as previously described by Moritz (1993) and Lim et al. (1989) *Proc. Natl. Acad. Sci., USA*, Vol. 86, p 8892. To stringently analyze transfer efficiency, only colonies expressing mADA at the same or a higher level than endogenous human ADA were considered transduced. For analysis of pooled colonies, colonies picked out of methylcellulose culture were combined in 1.5 ml microtubes (Rainin, Woburn, Mass.), washed with warm medium and phosphate buffered saline (PBS), centrifuged and stored at −20° C. For ADA analysis, cells were lysed in 5 microliter of lysis buffer by repeated freezing-thawing cycles and isoenzyme electrophoresis was performed as previously described.

2.3. Gene Transfer Efficiency into Committed Progenitor Cells

Transduction efficiency was compared by infecting bone marrow cells while plated on 30/35 FN- of BSA-coated dishes. No difference in the number of colonies obtained after infection without selection was observed between these conditions. As shown in Table 1, infection efficiency into all committed progenitors was substantially increased on 30/35 FN vs BSA. As expected with the high titer ($\sim 1\times 10^7$ virons/ml) vector, the transduction efficiency of committed progenitors was extremely high. Referring to Table I, infection of bone marrow on 30/35 FN with PGK-mADA yielded nearly 100% transduction of committed progenitors in two separate experiments.

TABLE 1

Infection efficiency of committed human progenitor cells on fibronectin 30/35 fragments using the PGK-mADA vector

| EXPERIMENT | BSA | 30/35FN |
|---|---|---|
| Exp 1 | 1/18* | 13/14 |
| Exp 2 | 2/13 | 12/13 |

*number of mADA expressing colonies/total colonies analyzed 2.4. Gene Transfer Efficiency into Long Term Culture-Initiating Cells In four independent experiments performed with PGK-mADA a significant proportion of progenitor colonies derived from 5 week old LTMC (i.e. LTC-IC derived colonies) expressed the transferred murine ADA gene. Expression ranged from 2/12 (17%) to 6/6 (100%) of analyzed colonies (Table 2). Expression of the introduced mADA gene exceeded or at least equaled the amount of endogenous human ADA activity in all colonies considered positive. Infection efficiency for PGK-MADA was higher than for TKNEO. As shown in Table 2, infection of bone marrow on 30/35 FN with PGK-MADA yielded nearly 100% transduction of committed progenitors in two separate experiments.

TABLE 2

Infection efficiency of human long term culture initiating cell (LTC-IC) using the PGK-mADA vector

| EXPERIMENT | BSA | 30/35FN |
|---|---|---|
| Exp 1 | 0/14* | 10/19 |
| Exp 2 | N/A | 2/12 |
| Exp 3 | 0/4 | 3/5 |
| Exp 4 | 0/4 | 6/6 |
| Total | 0/22 | 21/42 |

*number of mADA positive colonies/total colonies analyzed;
N/A: not analyzed 2.5. Specificity of 30/35 FN Effects on Infection Efficiency of Hematopoietic Cells Gene transfer efficiency into LTC-IC was increased on 30/35 FN. Due to the relatively small size of these secondary LTC-IC derived colonies, the ability to perform protein analysis on single colonies was limited. After infection with PGK-mADA on BSA, intact fibronectin and 42 FN 0/6, 0/4, and 0/3 LTC-IC-derived colonies, respectively, demonstrated expression of murine ADA, while 3/5 LTC-IC-derived colonies infected on 30/35 FN expressed mADA. In addition, when multiple LTC-IC-derived colonies were pooled before analysis in two additional experiments, mADA expression was detected only after infection on 30/35 FN and to a lesser degree on intact FN, but not on 42FN or BSA.

EXAMPLE 3

Gene Transfer into Bone Marrow Cells Using PGK-hADA 3.1. General Procedure

PGK-hADA virus supernatant is prepared as described for TKNEO in Example 1. Chymotryptic fragments of fibronectin (FIG. 1) are prepared as previously described in Example 1 and the retroviral infection protocol of Example 1 was followed. LTC-IC and methylcellulose assays were performed as described in Example 1.

3.2. Analysis of Retroviral Infection

For analysis of pooled colonies, colonies picked out of methylcellulose culture are combined in 1.5 ml microtubes (Rainin, Woburn, Mass.), washed with warm medium and PBS, centrifuged and stored at −20° C. For ADA analysis, cells are lysed in 5 microliter of lysis buffer by repeated freezing-thawing cycles and isoenzyme electrophoresis is performed as previously described.

EXAMPLE 4

Gene Transfer into Cord Blood Cells Using TKNEO 4.1. General Procedure

TKNEO virus supernatant and chymotryptic fragments of fibronectin (FIG. 1) were prepared as previously described in Example 1. The retroviral infection protocol in Example 1 was followed except that umbilical cord blood from normal, full term newborn infants was collected in tubes containing heparin according to protocols approved by the Institutional Review Board of Indiana University School of Medicine, and used instead of the bone marrow cells. LTC-IC (human stem cell) and methylcellulose assays were performed according to Example 1.

4.2. Gene Transfer Efficiency into Committed Progenitors

Infection on FN30/35 was more than four times increased compared to BSA in three separate experiments (Table 3).

TABLE 3

Infection Efficiency of Cord Blood Progenitor Cells Using 30/35 FN Fragment and TKNEO Vector

| | |
|---|---|
| BSA | 12 ± 17 |
| 30/35 | 55 ± 16 |

EXAMPLE 5

Gene Transfer into Cord Blood Cells Using PGK-mADA 5.1. General Procedure

PGK-mADA virus supernatant and chymotryptic fragments of fibronectin (FIG. 1) were prepared as previously described in Example 1. The retroviral infection protocol in Example 1 was followed except that cord blood from normal, full term newborn infants was collected in tubes containing heparin according to protocols approved by the Institutional Review Board of Indiana University School of Medicine. LTC-IC and methylcellulose assays were performed according to Example 1.

5.2. Gene Transfer Efficiency into Long-Term Culture Initiating Cells

Using the higher titer PGK-mADA vector, analysis of LTC-IC-derived colonies demonstrated high level expression of the introduced mADA cDNA only from cultures established from cord blood infected using supernatant on FN30/35. Little expression of mADA was detected in LTC-IC-derived colonies infected in BSA control plates.

The results shown in Examples 4 and 5 demonstrate that improved infection efficiency using FN30/35 can also be achieved when using cord blood progenitor and stem cells.

EXAMPLE 6

Gene Transfer into Cord Blood Cells Using PGK-hADA

PGK-hADA virus supernatant and chymotryptic fragments of fibronectin (FIG. 1) are prepared as described for TKNEO in Example 1. The retroviral infection protocol in Example 1 is followed except that cord blood from normal, full term newborn infants is collected in tubes containing heparin according to protocols approved by the Institutional Review Board of Indiana University School of Medicine, and used instead of the bone marrow cells. LTC-IC and methylcellulose assays are performed according to Example 1.

EXAMPLES 7–11

Retroviral Vectors and Producer Cell Lines for Examples 7–11.

For Examples 7–11, two retrovirus-producing packaging cell lines were employed: the ecotropic GP+E86 (Markowitz, D., S. Goff, and A. Bank, *J. Virol.*, Vol. 62, pp 1120–1124 (1988)) and the amphotropic GP+envAM12 cell lines (Markowitz, D., S. Goff, and A. Bank, *Virology*, Vol. 167, pp 400–406 (1988)), respectively. The retroviral vectors and producer clones used in studies described here are listed in Table 1.

TABLE 4

| VECTOR | PRODUCER/clone | cDNA expressed |
|---|---|---|
| PGK-hADA | GP + E86/EPHA-5 | human ADA |
| PM5neo | GP + E86/EAL2a | neo phosphotransferase, LAC-Z |
| TKNeo | GP + E86/TKNeo | neo phosphotransferase |
| PGK-mADA | GP + EnvAM12/55/6 | murine ADA |

All cell lines were cultured in Dulbecco's modified Eagles medium (DME, Gibco, Grand Island, N.Y.) containing 10% fetal calf serum (FCS, Hyclone, Logan, Utah) and 100 units/ml penicillin and 100 µg/ml streptomycin (P/S, both Gibco) except for EAL2a cells which were grown in DME-F12 (Gibco) with 10% FCS plus P/S. Virus containing supernatant was collected by adding 10 ml of alpha-minimal essential medium (αMEM, Gibco) for murine cells or Iscove's Dulbecco Medium (IMDM, Gibco) for human cells each containing 10% FCS plus P/S to confluent 10 cm plates overnight. Harvested medium was filtered through 0.45 micron filters (Gelman Sciences, Ann Arbor, Mich.) and stored at −80° until used.

EXAMPLE 7

Transduction of Primary Murine Hematopoietic Cells 7.1. Experimental

For studies with murine cells, bone marrow was harvested from femurs and tibiae of 6 to 8 week old C3H/HeJ mice 2 days following administration of 150 mg/kg 5-fluorouracil (SoloPack Laboratories, Franklin Park, Ill.) (Lim, B., J. F. Apperley, S. H. Orkin, and D. A. Williams, *Proc. Natl. Acad. Sci. USA*, Vol. 86, pp 8892–8896 (1989)). Cells were pre-stimulated at a concentration of $5 \times 10^5$ cells/ml in IMDM/20% FCS plus P/S with 100 ng/ml rat recombinant stem cell factor (rrSCF; Amgen, Thousands Oaks, Calif.) and 100 units/ml recombinant human interlukin-6 (rhIL-6; Pepro Tech Inc., Rock Hill, N.J.) for 48 hours (Luskey, B. D., M. Rosenblatt, K. Zsebo, and D. A. Williams, *Blood*, Vol. 80, pp 396–402 (1992)). Subsequently, gene transfer efficiency with the PGK-hADA vector produced by EPHA-5 producer cells was compared using three different infection protocols: 1) supernatant infection; 2) supernatant infection on FN 30/35; 3) cocultivation on EPHA-5 producer cells. Therefore, 100 mm bacterial dishes were coated with 2.5 µg/cm$^2$ FN 30/35 (equivalent to 75 pmol/cm$^2$) dissolved in 5 ml phosphate buffered saline (PBS; Gibco) for 1 hour at room temperature under UV light with the dish lid open and for another hour with the dish lid closed. After blocking with 2% bovine serum albumin (BSA, Fraction V; Boehringer Mannheim, Indianapolis, Ind.) for 30 minutes at room temperature, dishes were washed once with Hank's Balanced Salt Solution (HBSS) supplemented with 2.5% (v/v) 1M Hepes (both Gibco). For supernatant infection, dishes were coated with BSA only. 5×10$^6$ prestimulated donor cells were incubated with 10 ml of virus supernatant obtained from EPHA-5 cells as described above supplemented with 100 U/ml rhIL-6, 100 ng/ml hrSCF and 7.5 µg/ml polybrene. Non-adherent cells were collected and re-added with the fresh virus supernatant. For co-culture, EPHA-5 cells in 4 ml medium were incubated with 10 µg/ml mitomycin C for 2 hours at 37° C., washed, trypsinized and seeded on 100 mm tissue culture dishes at a concentration of 3×10$^6$ cells in 10 ml αMEM/20% FCS plus P/S. The next day, 5×10$^6$ prestimulated bone marrow cells with 100 U/ml rhIL-6, 100 ng/ml rrSCF and 4 µg/ml polybrene were added for 48 hours. Following the infection protocol, non-adherent cells were decanted and adherent hematopoietic cells were collected from the cultures using Cell Dissociation Buffer (CDB) (enzyme free/PBS based, Gibco) according to the manufacturer's instructions. The adherent cells were added to the non-adherent fraction, washed twice, and suspended in approximately 1 ml of HBSS/Hepes. The total cells obtained from 5×10$^6$ prestimulated cells were injected into the tail veins of three recipient mice which had been subjected to lethal total body irradiation (with 700 plus 400 cGy, $^{137}$Cs-source) (Luskey, B. D., M. Rosenblatt, K. Zsebo, and D. A. Williams, *Blood*, Vol. 80, pp 396–402 (1992)). The transduction of hematopoietic stem cells was analyzed by examination of reconstituted mice for the expression of the introduced human ADA cDNA. This ADA isoenzyme analysis was performed in transplanted mice by examining peripheral blood cells for the presence of the hADA protein by cellulose acetate in situ enzyme analysis (Lim, B., D. A. Williams, and S. H. Orkin, *Mol. Cell. Biol.*, Vol. 7, pp 3459–3465 (1987)). Examination was performed beginning 4 months post-transplant and was repeated monthly.

7.2 Results

Figure 4:
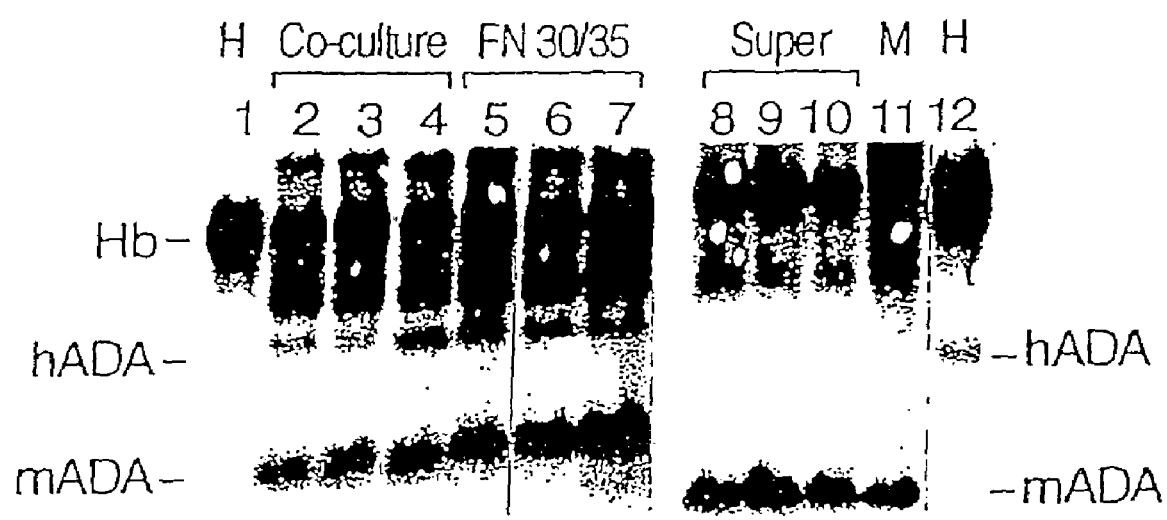
FIG. 4 compares the presence of hADA in mice engrafted with bone marrow cells transduced by (i) the coculture method (lanes 2–4), (ii) supernatant infection in the presence of immobilized fibronectin fragments (lanes 5–7), and supernatant infection on BSA (lanes 8–10), as further described in Example 7, infra. Controls for hADA are shown in lanes 1 and 12 and for murine ADA in lane 11.

Long-term bone marrow reconstitution of mice with genetically manipulated hematopoietic stem cells is generally accepted as adequate to determine the efficiency of stem cell transduction after a period of 4 months post-transplant. Analysis of recipients of transduced bone marrow after 7 months by isoenzyme analysis revealed that: 1) human ADA cDNA expression was present using either co-culture or supernatant infection on FN 30/35 but absent in the group transplanted after supernatant infection without FN 30/35 and that; 2) the levels of expression were comparable for the co-culture and FN 30/35 groups. As shown in FIG. 4, lanes 2–4, three mice transplanted with bone marrow transduced by co-culture on EPHA-5 cells demonstrated easily detectable human ADA. Similar levels of human ADA were detected in three mice transplanted with hematopoietic cells transduced by supernatant infection of FN 20/35 (FIG. 4, lanes 5–7). In contrast, no human ADA was detected in three mice transplanted with hematopoietic cells transduced by supernatant infection on BSA (FIG. 4, lanes 8–10). Controls for the location of human ADA are shown in lanes 1 and 12 and murine ADA in lane 11 of FIG. 4. The murine band in lanes 2–10 reveals that equal amounts of protein were loaded. These data demonstrate that transduction of long-term reconstituting hematopoietic stem cells by supernatant infection on FN 30/35 is equivalent to co-culture and far superior to supernatant infection without FN 30/35.

EXAMPLE 8

Mechanism of Improved Transduction by Retrovirus Vectors Binding to FN 30/35

8.1. Experimental

To test whether increased transduction is the result of co-localization of virus and hematopoietic cells, we analyzed whether recombinant retroviral particles demonstrate binding to FN 30/35. Therefore, FN 30/35-coated plates were preincubated with supernatant containing TKNeo virus for 30 minutes and thereafter extensively washed. The viral titer of supernatant was determined using NIH/3T3 cells according to standard procedures (Markowitz, D., S. Goff, and A. Bank, *J. Virol.*, Vol. 62, pp 1120–1124 (1988)). Briefly, 3T3 cells were plated at a concentration of 1000 cells/well in a 6-well tissue culture plate and grown overnight. Serial dilutions of virus supernatant were added to each well with 7.5 µ/ml polybrene and incubated for 2.5 hours at 37° C. after which 2 ml of medium was added. After 24 hours, the medium was replaced with medium containing G418 (0.75 mg/ml, dry powder, Gibco) and the plates incubated for 10–12 days. The G418-resistant colonies (G418$^r$ were stained after 10–12 days and scored. The number of colonies/well multiplied by the dilution of virus supernatant was used as the infectious particles (cfu)/ml of supernatant. We assessed/"titered" the amount of retroviral particles remaining on FN 30/35-coated or BSA-coated 35 mm plates after preincubation with virus supernatant and intensive washing by adding 1000 NIH/3T3 per 35 mm bacteriologic dish cells plus polybrene. Twenty-four hours later, cultures were fed with medium containing 0.75 mg/ml G418 (dry powder) and the cells further incubated for 10–12 days. Following this incubation, the presence of adherent virus was quantitated by enumerating G418-resistant NIH/3T3 colonies.

To assess whether virus binding to FN 30/35 occurs in a dose-dependent fashion, the above experiments were repeated with increasing concentrations of FN 30/35 coating the dishes. Therefore, 35 mm bacteriologic dishes were coated with 1, 4, 10 and 20 µg/cm$^2$ FN 30/35 as described above. A 1:50 dilution of a TKNeo virus stock previously titered at 1×10$^4$ infectious particles/ml was incubated on FN 30/35-coated plates for 30 minutes. After intensive washing, 2000 NIH/3T3 cells were added to each well. Selection was carried out as above and G418-resistant NIH/3T3 colonies counted after 10 days of selection.

8.2. Results

Figure 5:
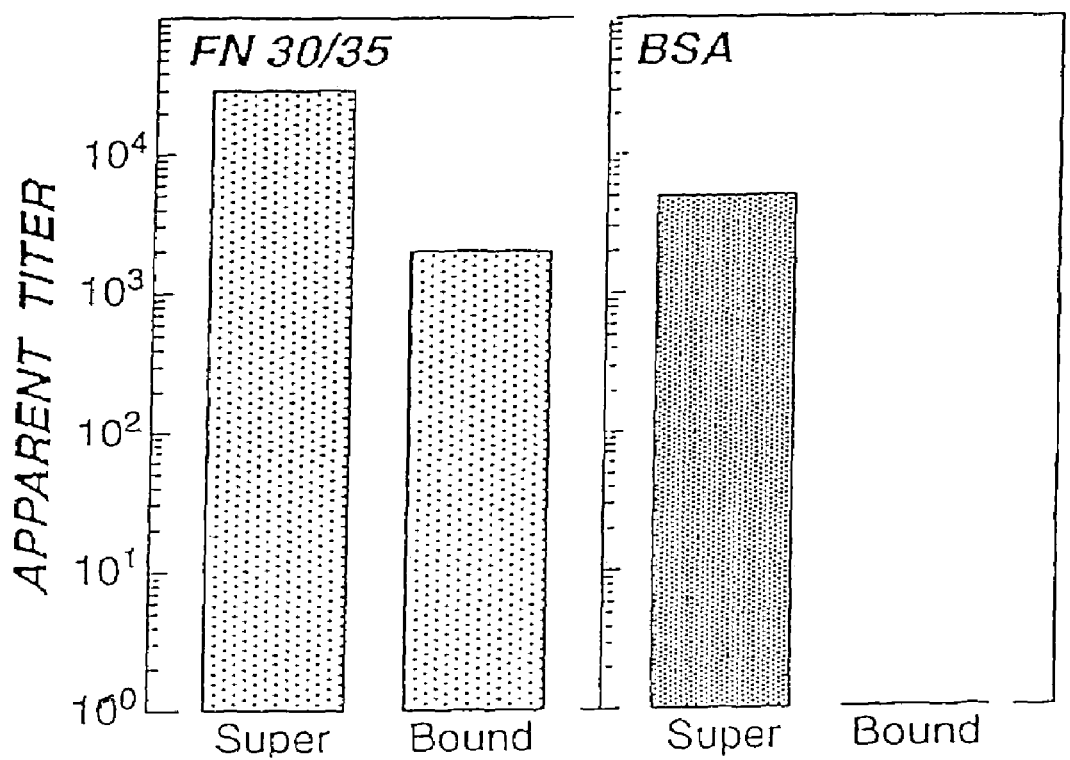
FIG. 5 demonstrates retroviral binding to fibronectin fragments, as further described in Example 8, infra.
Figure 6:
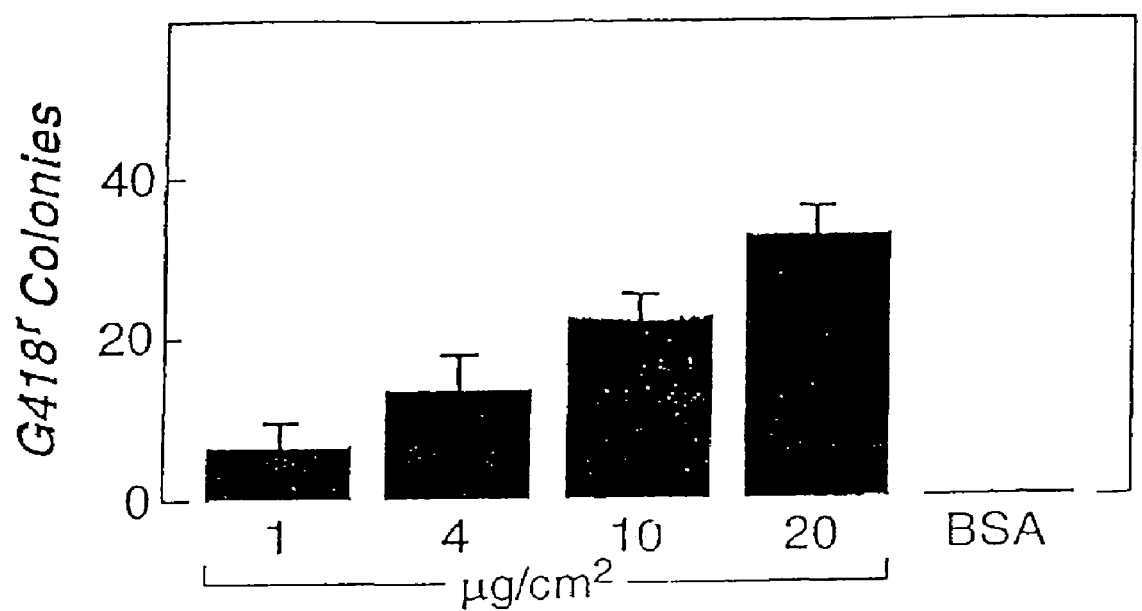
FIG. 6 demonstrates that retroviral binding to fibronectin fragments is dose-dependent, as further described in Example 8, infra.

FIG. 5 sets forth the results of one of three representative experiments. Using TKNeo supernatant, retroviral titers measured by G418$^r$ colonies in NIH/3T3 cells were reduced by more than 3 logs (4×10$^3$ to 0) on BSA-coated plates, while titer reduction was only 1 log on plates coated with 30/35 FN. These data demonstrate that retrovirus quantitatively binds to FN 30/35 but does not bind to dishes coated with BSA (control dishes). FIG. 6 shows that increased numbers of G418-resistant colonies were detected when virus-containing supernatant was incubated on plates coated with increased concentrations of FN 30/35. Therefore, virus binding to FN 30/35 occurs in a dose-dependent fashion.

EXAMPLE 9

Virus Binding to Recombinant Fibronectin Fragments 9.1. Experimental

Figure 7:
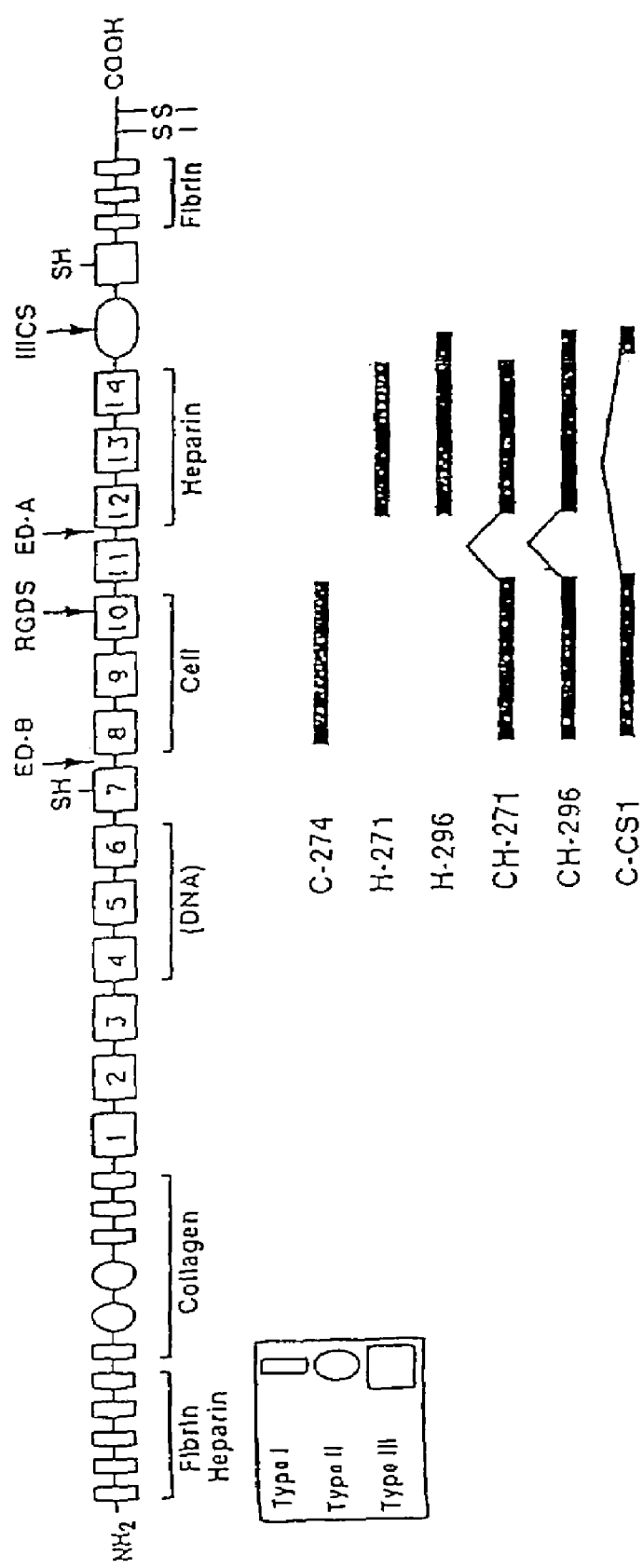
FIG. 7 provides a schematic diagram illustrating various recombinant fibronectin fragments used in Examples 9–11, infra.

Kimizuka et al. have previously reported the expression of cloned FN DNA sequences in *E. coli* (Kimizuka, F., Y. Taguchi, Y. Ohdate, Y. Kawase, T. Shimojo, D. Hashino, I. Kato, K. Sekiguchi, and K. Titani, *J. Biochem.*, Vol. 110, pp 284–291 (1991)). Cloned and chimeric peptides include one or a combination of several important sequences in fibronectin known to participate in cell adhesion (including RGDS, CS-1 and heparin-binding site), see FIG. 7. To analyze whether retrovirus can bind to these recombinant FN fragments, 3T3 cell colony formation assays were repeated on plates coated with the recombinant fragments C-274, H-271, H-296, CH-271, CH-296, and CS-1 as well as FN 30/35 as a positive control, using two different dilutions (1:10 and 1:100) of the frozen retrovirus TKNeo stock with $1 \times 10^4$ infectious particles/ml. FN fragments were used at a concentration of 120–130 pmol/cm$^2$ (equivalent to 4 µg/cm$^2$ for C-274, H-271, H-296, C-CS1, FN 30/35 and 8 µg/cm$^2$ for CH-271 and CH-296). Briefly, plates were coated, virus was added, plates were extensively washed, NIH/3T3 cells were added for 24 hours and then grown in selection medium for 10 days, subsequently colonies were stained and counted.

9.2. Results

Figure 8:
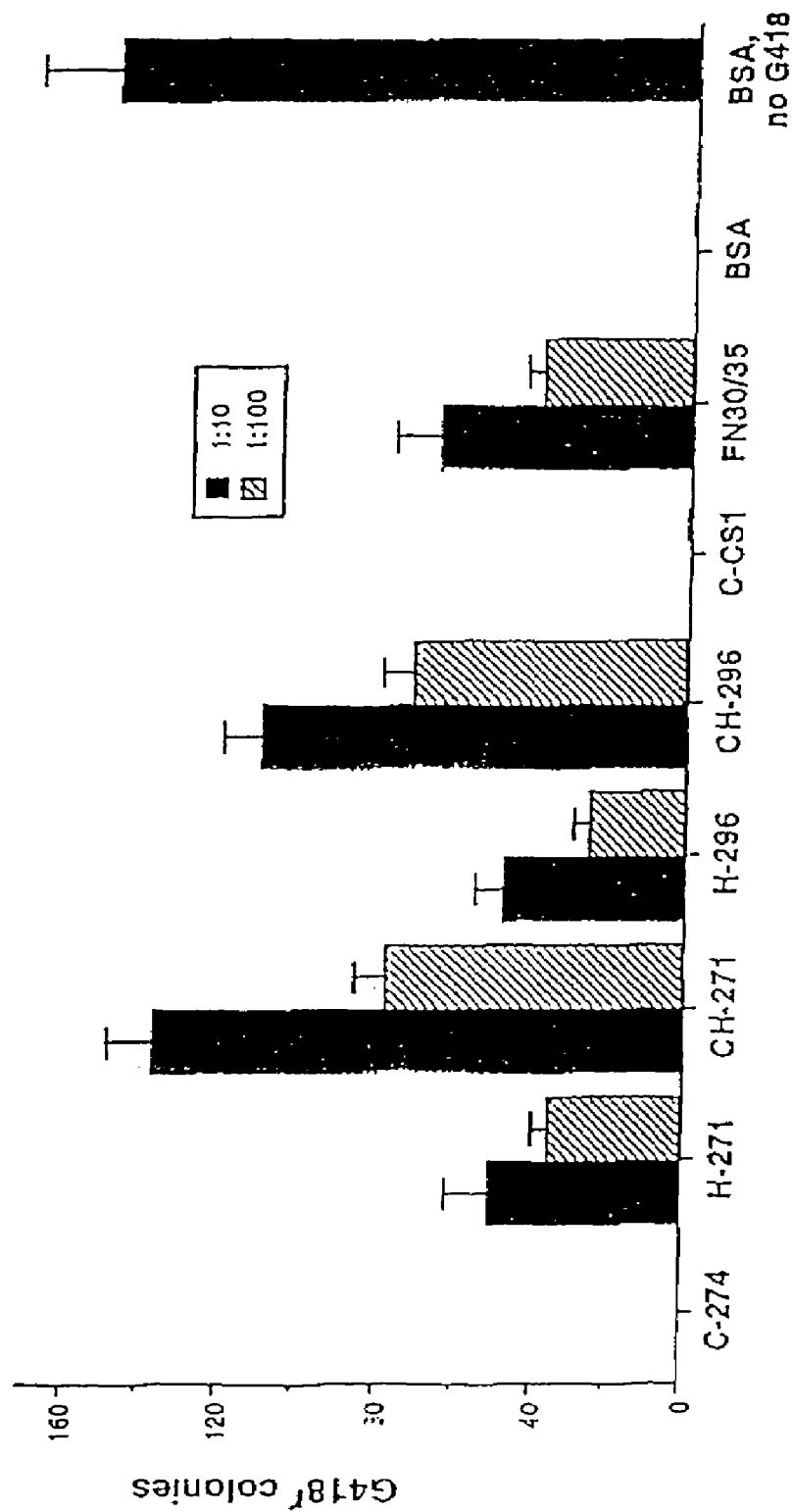
FIG. 8 shows retrovirus binding to various fibronectin fragments, including to several recombinant fragments, as described in Example 9, infra.
Figure 9:
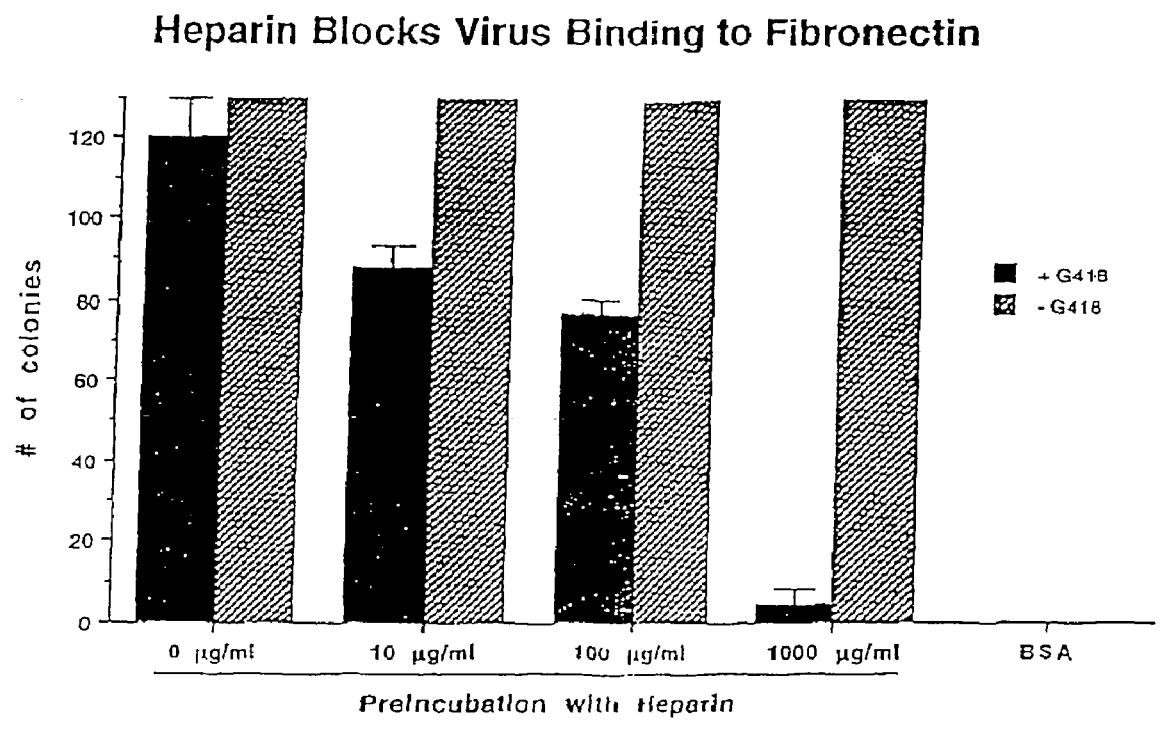

FIG. 8 demonstrates that the number of the G418-resistant colonies (and therefore virus adhesion) was increased in fragments H-271, H-296, CH-271 and CH-296. Furthermore, it shows that the amount of virus bound was roughly comparable between these recombinant fragments and FN 30/35, although in this work the CH-271 fragment exhibited the highest level of virus binding. Common to all of these 5 FN fragments are the type III repeats 12–14 which contain the high-affinity heparin-binding site (Ruoslahti, E., *Ann. Rev. Biochem.*, Vol. 57, pp 375–413 (1988) and Kimizuka, F., Y. Taguchi, Y. Ohdate, Y. Kawase, T. Shimojo, K. Hashino, I. Kato, K. Sekiguchi, and K. Titani, *J. Biochem.*, Vol. 110, pp 284–291 (1991)) probably located in repeat 13 (Kimizuka, F., Y. Taguchi, Y. Ohdate, Y. Kawase, T. Shimojo, K. Hashino, I. Kato, K. Sekiguchi, and K. Titani, *J. Biochem.*, Vol. 110, pp 284–291 (1991)). This suggests that virus binding is occurring via this known adhesion site. This was evidenced by pre-incubating dishes coated with 4 µg/cm$^2$ CH-271 with increasing concentrations (10–1000 µg/ml) of heparin sulfate, a highly charged molecule known to inhibit cell binding to the heparin-binding site. As seen in FIG. 9, the number of G418-resistant colonies is decreased following pre-incubation of CH-271 with increasing concentrations of heparin sulfate. These data suggest that virus binding to FN is mediated through the high affinity heparin-binding site located immediately adjacent to the CS-1 site in the carboxyl-terminal domains of FN.

EXAMPLE 10

Transduction of Hematopoietic Cells on Recombinant Fibronectin Fragments 10.1. Experimental To analyze whether the increased transduction of hematopoietic cells described previously on FN 30/35 could also be seen with recombinant FN fragments, we assessed the transduction efficiency of supernatant infections in vitro using high proliferative potential-colony forming cell (HPP-CFC) assays. By employing EAL2a vectors, we compared the influence of various recombinant FN fragments versus FN 30/35 supernatant infection on BSA on transduction of hematopoietic cells using growth of G418-resistant colonies as an indicator of gene transfer. Furthermore, we compared the ability of virus particles already adherent to FN fragments (versus supernatant virus) to transduce hematopoietic cells. 0.5 to $1 \times 10^6$ prestimulated bone marrow cells were incubated on 35 mm FN-coated petri dishes in 1–2 ml of EAL2a virus containing supernatant with growth factors and 5 µg/ml polybrene as discussed above. To assess transduction of hematopoietic cells by virus bound to FN fragments, 35 mm FN-coated dishes incubated with virus-containing supernatant were washed three times with 2 ml PBS each. Subsequently, 0.5 to $1 \times 10^6$ prestimulated bone barrow cells were added in 2 ml of medium supplemented with growth factors and polybrene. 22 hours later, cells were harvested and plated in HPP-CFC assays with and without 1.5 mg/ml G418 as described (Bradley, T. R. and D. Metcalf, *Aust. J. Exp. Biol. Med. Sci.*, Vol. 44, pp 287–293 (1966)). The cultures were incubated for 14 days in 7% CO$_2$ at 33° C. and the gene transfer efficiency was calculated as the percentage of G418 resistant colonies.

10.2. Results

Figure 10:
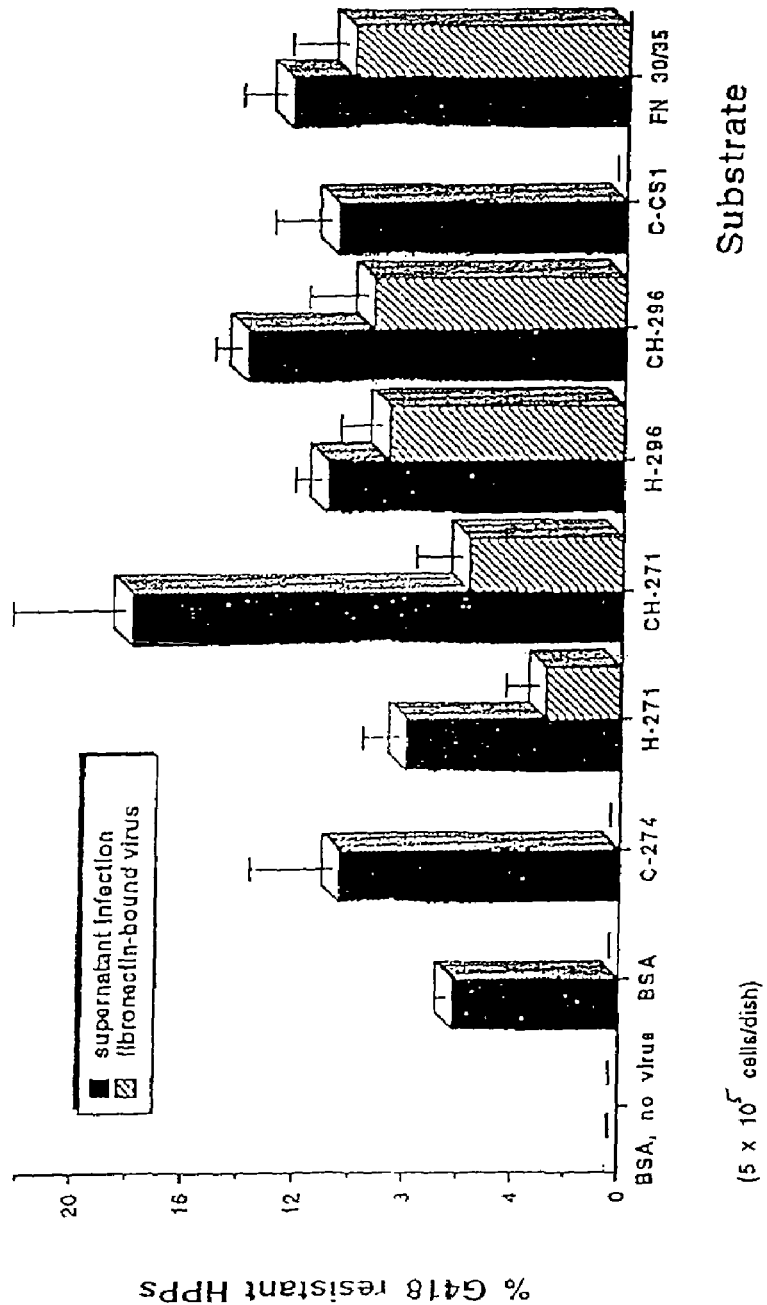
FIG. 10 shows the efficiency of retrovirus infection of murine hematopoietic cells in the presence of various fibronectin fragments, as further reported in Example 10, infra.

Transduction of primitive hematopoietic cells via supernatant infection (FIG. 10) was significantly higher than supernatant infection on BSA for all fragments which included the heparin-binding site (HBS) and at least one more active cell adhesion site (solid bars). Transduction efficacy of the recombinant fragments CH-271, H-296, CH-296 and C-CS1 was similar to the effect of FN 30/35, all three fragments which include both the heparin-binding and the CS-1 site. In all other cases the transduction was dramatically reduced. These data demonstrate that the increased transduction of primitive hematopoietic cells previously shown on FN 30/35 can be replicated on recombinant FN fragments. It further demonstrates that virus directly bound to fibronectin is capable of genetic transduction of hematopoietic cells. Finally it confirms the utility of the presence of both the CS-1 and the heparin binding site for transduction of primitive hematopoietic precursor (stem) cells.

EXAMPLE 11

Long-Term Bone Marrow Reconstitution of Mice Using Transduction of Murine Donor Cells on Recombinant Fibronectin Fragments 11.1. Experimental We repeated the above in vitro studies (from Example 10) for primitive hematopoietic progenitor cells comparing supernatant infection on BSA vs FN 30/35 versus recombinant FN fragments versus coculture using bone marrow transplantation to analyze effects on reconstituting hematopoietic stem cells. Briefly, lethally irradiated mice were injected with donor cells which were transduced with the EPHA-5 vectors containing the human ADA cDNA. After 1 month and after approximately 6 months, gene transfer efficacy was analyzed from peripheral blood in ADA isoenzyme assays.

11.2. Results

Figure 11:
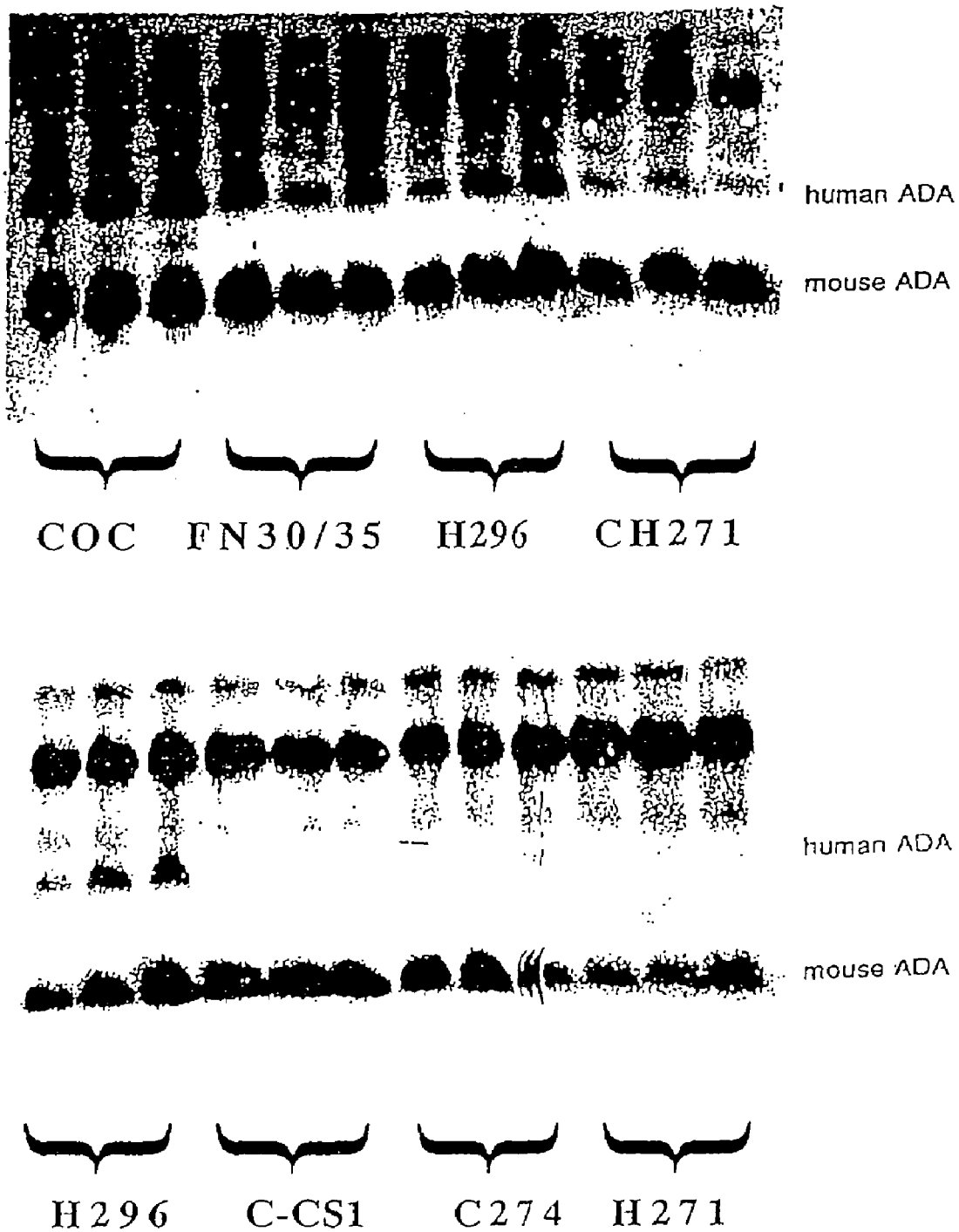

FIG. 11 shows results after 1 month, and clearly shows the fibronectin fragment H-296 containing both the heparin binding site and the CS-1 yields similar results to FN 30/35 and coculture. Fragments which do not contain both these sites are less effective in transducing a transplantable hematopoietic cell. These data demonstrate that co-localization of primitive hematopoietic/stem cells and retrovirus bound to recombinant FN fragments containing both the CS-1 and the heparin binding sites effectively transduces transplantable hematopoietic cells.

Figure 12:
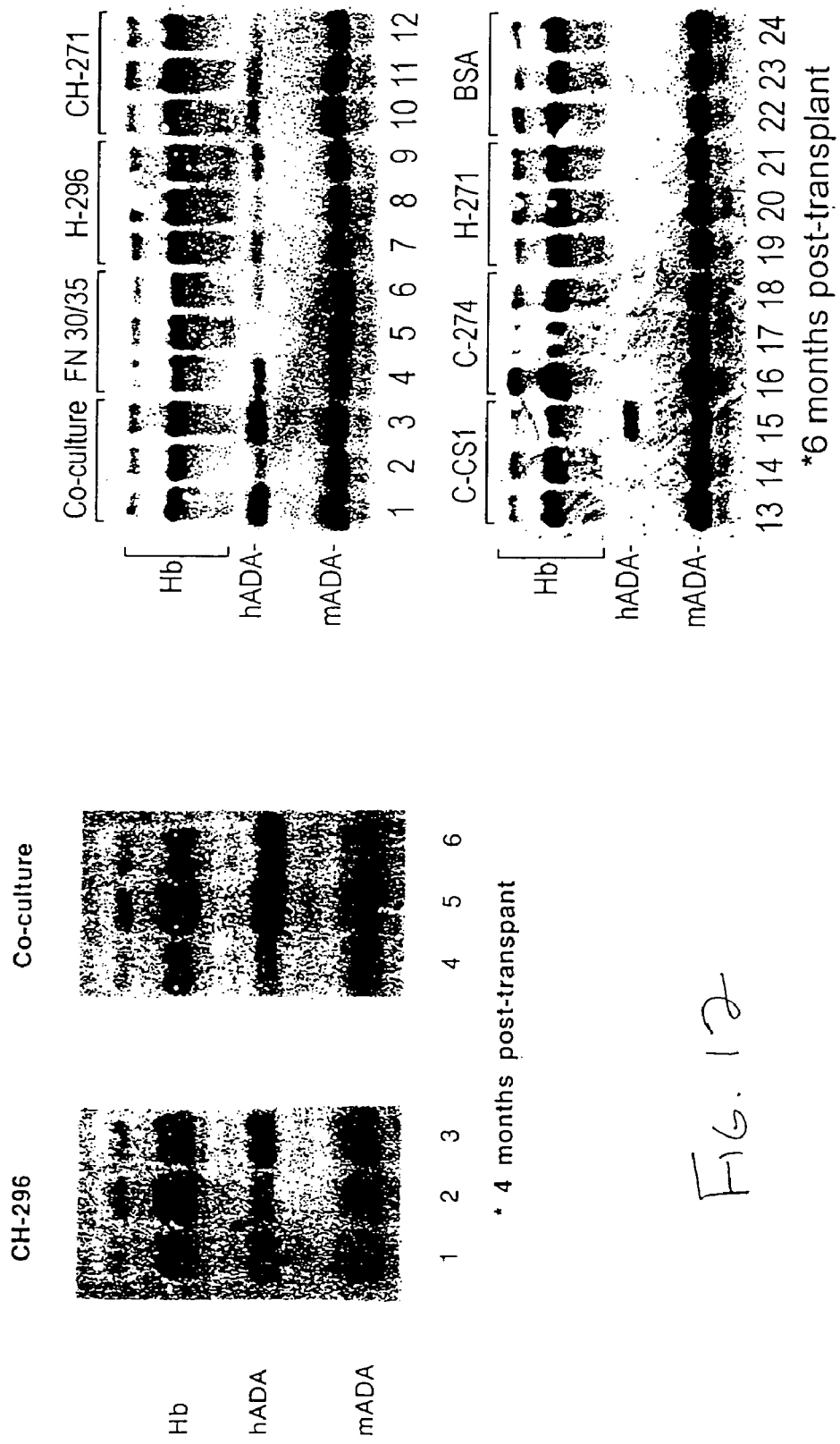

FIG. 12 shows results four and six months post-transplantation. At this time point, genetic transduction of repopulating hematopoietic stem cells could not be demonstrated in animals transplanted with cells transduced on control plates or on fragments containing only CBD (C-274) or $III_{12-14}$ (H-271). Genetic transduction of HSCs was less frequently seen on the C-CS1 fragment, in this case ⅓ animals was positive for the human protein. Gene transfer in in vivo repopulating stem cells was uniformly seen on fragments containing the HBD in combination with either CBD (CH-271) or CS1 (H-296). Transduction on fragments containing all three cell binding sites (CH-296) was most efficient comparable with co-culture of target cells the producer cell line. These data show that fibronectin fragments which contain $III_{12-14}$ in combination with the binding site(s) for VLA-4 and/or VLA-5 are capable of increasing retroviral-mediated gene transfer into murine hematopoietic progenitor and stem cells.

EXAMPLE 12

Fibronectin directs cell adhesion through at least three sites (FIG. 13): the cell binding domain (CBD) which contains the tetrapeptide RGDS in repeat 10 via the integrin VLA-5; the heparin binding domain contained within the type III repeats 12-14 ($III_{12-14}$) via cell surface proteoglycan molecules; and the CS1 sequence within the alternatively spliced IIICS region via the integrin VLA-4. In these studies, we utilized six chimeric recombinant FN fragments shown in FIG. 13 which contain these single cell adhesion sites alone or in combinations in the peptide.

FN-coated bacterial dishes were incubated with 200 cfu in 2 ml of supernatent (SN) from the amphotropic packaging cell line TKNeo. After 30 minutes at 37° C., dishes were washed three times with PBS and then 2000 NIH/3T3 (fibroblast) cells were added in 2 ml of DMEM supplemented with 10% calf serum (CS; Sigma, U.S.A.) and 2% P/S. The next day, cells were put in selection medium with 0.75 mg/ml G418. 8–10 days later, dishes were stained with Stat Stain (Volu-Sol, U.S.A.) and $G418^r$ colonies counted. By this assay, retrovirus does not bind to uncoated or BSA-coated plates. As shown in FIG. 14, gene transfer into NIH/3T3 cells occurred only on fragments which contained the Heparin-II binding domain, also referred to herein as "$III_{12-14}$" (H-271, CH-271, H-296, CH-296). These data demonstrate that retroviral particles directly bind to sequences within the $III_{12-14}$ repeats of fibronectin. Infection of NIH/3T3 cells was significantly higher on FN fragments containing both $III_{12-14}$ and CBD compared to $III_{12-14}$ alone (compare H-271 versus CH-271). Remarkably, up to 80 $G418^r$ NIH/3T3 colonies/plate were generated from an input of only 200 NEO cfu/plate. In contrast, addition of CS1 did not show any effect on NIH/3T3 transduction (H-271 versus H-296, CH-271 versus CH-296).

To evidence that the mechanism by which FN increased retroviral-mediated gene transfer is by the simultaneous binding of retrovirus and target cells to the fragment, experiments using a non-adherent cell line (HL60—a known promyelocytic leukemia cell line) were conducted. HL60 cells were stained with directly fluorochrome-conjugated monoclonal antibodies against VLA-4 (FITC; Immunotech, U.S.A.) and VLA-5 (PE; Antigenix America, U.S.A.) or with the isotype controls for IgG1 and IgG2a (Becton Dickinson). Dead cells were excluded by propifium iodine staining. Cells were then analyzed on a FACScan (Becton Dickinson). For gene transfer studies, $10^4$ HL60 cells were suspended with viral supernatant from the amphotropic packaging cell line DAG (obtained from St. Jude's Children Research Hospital, Memphis, Tenn., U.S.A.) containing the extracellular domain of the nerve growth factor receptor (NGF-R) (titer $10^5$ cfu/ml) and then added to bacterial 6-well plates coated with the six FN fragments at a concentration of 2 μg/cm². After 4 hours, 2 ml of conditioned medium from ongoing HL60 cultures was added. 4 ml of fresh medium (RPMI (Gibco) with 5% FCS and 2% P/S) was added after 4–5 days. Cells were allowed to grow for a total of 8 days and then stained with the monoclonal antibody 8211 against the NGF-R (Boehringer, U.S.A.) or with an isotype IgG1 control (Dako, U.S.A.) and then reacted with a secondary FITC-conjugated goat-anti-mouse serum (Boehringer). Samples were incubated with propidium iodine (PI) for exclusion of cell debris and subsequently measured on the FACScan. Gene transfer was demonstrated after gating for live cells by analysis of the NGF-R expression. All gene transfer studies were performed without Polybrene or protamine. As shown in FIG. 15, HL60 cells express VLA-4 but not VLA-5 in flow cytometry analysis (A+B). Consistent with expression data, HL60 cells adhered only to plates coated with fragments containing CS1 (H-296, CH-296, C-CS1). As shown in FIG. 15, genetic transduction of HL-60 cells occurred only on fragments which contained $III_{12-14}$ in combination with CS1 (H-296, CH-296). Although HL-60 cells adhere to the C-CS1 fragment via their VLA-4 integrin, the absence of $III_{12-14}$ to which retroviral binding occurs dramatically reduces transduction of HL60 cells.

In another set of experiments, increasing concentration of high molecular weight (HMW) heparin (Sigma, U.S.A., MW about 7000–25000) were dissolved in 2 ml Hanks Balanced Salt Solution supplemented with 2.5% (v/v) 1 M Hepes (HBSS/Hepes; all Gibco) and added to bacterial 6-well plates coated with the different FN fragments at a concentration of 4 μg/cm². After 30 minutes plates were washed three times with PBS and then 400 cfu/2 ml of the amphotropic TKNeo vector was added. After 30 minutes at 37° C., plates were washed again with PBS and then 2000 NIH/3T3 cells in DMEM with 10% CS and 2% P/S were added. Selection was performed as above and gene transfer efficiency was enumerated as the number of G418$^r$ colonies after 8–10 days of culture. In a similar set of experiments, fractionated low molecular weight (LMW) heparin (Sigma, U.S.A., MW about 3000) was dissolved in 2 ml of HBSS/Hepes at increasing concentration. Experimental design was then as described above for HMW heparin. Gene transfer efficiency was read out as the number of G418r colonies after 8–10 days. All of these gene transfer studies were performed without Polybrene or protamine. The results of these experiments are shown in FIG. 16. As shown, virus binding to FN can be competed in a dose-dependent fashion by high (16A), but not low molecular weight heparin (16B). These results evidence that retroviral particles bind to sequences within $III_{12-14}$.

EXAMPLE 13

Selective Transduction of BFU-E Cells in CD34+ Cellular Population

In this Example it was demonstrated that selected cells within a mixed cellular population can be targeted for transduction by using a polypeptide with a viral binding domain and a cell binding domain which is specific for the targeted cells. The general TKNEO infection and assay protocols of Example 1 were repeated, except using a substantially homogeneous population of CD34+ cells containing BFU-E, CFU-GM and CFU-Mix cells (obtained by affinity chromatography from cord blood (CB) cells), and using the recombinant FN fragment CH-271 at varied concentrations of 1, 2, 4, 8, 16 and 20 μg/cm². The results are shown in FIG. 17. As shown, BFU-E cells, which bind to the VLA-5 binding site, were transduced with high efficiencies (greater than 25% G418 resistant colonies), whereas CFU-GM and CFU-Mix populations, which do not exhibit significant binding to VLA-5, were transduced at substantially lower efficiencies (less than about 5% G418 resistant colonies).

EXAMPLE 14

Transduction of c-KIT+ Cells

In this Example a cellular population substantially homogeneous as to c-KIT+ was transduced in accordance with the invention. Thus, c-KIT+ cells were isolated from murine bone marrow using flow cytometric sorting techniques. The cells were subjected to an infection protocol using the TKNEO vector generally as described in Example 1 except varying the FN fragment as indicated in FIG. 18, and the infected cells were assayed for HPP-CFC. As shown in FIG. 18, FN fragments which contained $III_{12-14}$ and the VLA-4 binding site (FN 30/35, H296, and CH-296) led to high transduction efficiencies (greater than 80% G418 resistant colonies) whereas FN fragments lacking these two domains resulted in no significant transduction (C274 and C-CS1) or substantially lower efficiencies (H271, CH271, less than 20% G418 resistant colonies).

EXAMPLE 15

Transduction of NIH/3T3 and Clonogenic BM Cells Using Varying Concentrations of Polybrene In this set of experiments it was demonstrated that advantageous transduction methods of the invention are conducted in the absence of hexadimethrine bromide. NIH/3T3 (fibroblast) cells and clonogenic bone marrow cells were subjected to TKNEO infection protocols generally as described in Examples 12 and 1, respectively, except that the vector, cells and varying concentrations of Polybrene were first suspended together and then applied to a substrate coated with the FN fragment CH-296 (8 μg/ml). Assays were as described previously for these cell types. The results are given in FIGS. 19 and 20. As shown in FIG. 19, the number of G418 resistant NIH/3T3 colonies decreases dramatically with increasing Polybrene concentrations, ranging from about 14 when no Polybrene was used down to about 4 when 12.5 μg/ml Polybrene was used. Similarly, FIG. 20 reflects that nearly 40 colonies were observed when the protocol was conducted in the absence of Polybrene, whereas the corresponding value when using 10 μg/ml was less than 15.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

All publications cited herein are hereby incorporated by reference in their entirety as if each had been individually incorporated by reference and fully set forth. In addition, co-pending U.S. patent application Ser. No. 08/218,355 filed Mar. 25, 1994, and co-pending International Application Serial No. PCT/US95/03817 filed Mar. 27, 1995 and designating the United States, are hereby incorporated by reference in their entirety as is fully set forth.

What is claimed is:

1. A method for transduction of hematopoietic cells by a replication-defective recombinant retrovirus vector, comprising infecting viable hematopoietic cells in culture with a replication-defective recombinant retrovirus in the presence of substantially pure fibronectin, substantially pure fibronectin fragments, or a mixture thereof, to produce transduced hematopoietic cells, said fibronectin and said fibronectin fragments containing the alternatively spliced CS-1 cell adhesion domain and the Heparin II binding domain of fibronectin.

2. The method of claim 1 which includes harvesting the transduced hematopoietic cells.

3. The method of claim 1 wherein the hematopoietic cells have a protein deficiency or abnormality and the recombinant retrovirus vector includes an exogenous gene encoding the protein.

4. The method of claim 1 wherein the hematopoietic cells have an enzyme deficiency or abnormality and the exogenous gene is a gene encoding the enzyme.

5. The method of claim 4 wherein the hematopoietic cells are human hematopoietic cells having an enzyme deficiency or abnormality and the exogenous gene is a human gene encoding the enzyme.

6. The method of claim 4 wherein the hematopoietic cells have an adenosine deaminase deficiency and the exogenous gene encodes adenosine deaminase.

7. The method of claim 5 wherein the human hematopoietic cells have an adenosine deaminase deficiency and the exogenous gene encodes adenosine deaminase.

8. The method of claim 5 wherein the cells are infected with the retrovirus in the presence of an immobilized fibronectin fragment containing an amino acid sequence which provides the cell-binding activity of the CS-1 domain and an amino acid sequence which provides the retrovirus binding activity of the Heparin-II domain.

9. The method of claim 8 wherein the fibronectin fragment is a recombinant fibronectin fragment.

10. The method of claim 9, wherein the recombinant fibronectin fragment is selected from the group consisting of H-296 and CH-296.

11. The method of claim 10, wherein the recombinant fibronectin fragment is CH-296.

12. The method of claim 9, wherein the recombinant fibronectin fragment contains the Heparin-II binding domain of fibronectin.

13. The method of claim 1, wherein the hematopoietic cells are characterized as adherent-negative, low density, mononuclear cells.

14. A method for transduction of viable mammalian cells by a replication-defective recombinant retrovirus vector, comprising infecting the cells in culture with a replication-defective recombinant retrovirus in the presence of substantially pure fibronectin, substantially pure fibronectin fragments, or a mixture thereof, without cocultivation with retrovirus producing cells to produce transduced cells.

15. The method of claim 14, wherein the infecting is in the presence of a fibronectin fragment containing the Heparin-II binding domain of fibronectin.

16. The method of claim 15, wherein said domain has an amino acid sequence represented by the formula (SEQ. ID NO. 1):

```
Ala Ile Pro Ala Pro Thr Asp Leu Lys Phe Thr Gln Val Thr Pro Thr Ser Leu Ser Ala Gln Trp Thr

Pro Pro Asn Val Gln Leu Thr Gly Tyr Arg Val Arg Val Thr Pro Lys Glu Lys Thr Gly Pro Met

Lys Glu Ile Asn Leu Ala Pro Asp Ser Ser Ser Val Val Val Ser Gly Leu Met Val Ala Thr Lys Tyr

Glu Val Ser Val Tyr Ala Leu Lys Asp Thr Leu Thr Ser Arg Pro Ala Gln Gly Val Val Thr Thr

Leu Glu Asn Val Ser Pro Pro Arg Arg Ala Arg Val Thr Asp Ala Thr Glu Thr Thr Ile Thr Ile Ser

Trp Arg Thr Lys Thr Glu Thr Ile Thr Gly Phe Gln Val Asp Ala Val Pro Ala Asn Gly Gln Thr Pro

Ile Gln Arg Thr Ile Lys Pro Asp Val Arg Ser Tyr Thr Ile Thr Gly Leu Gln Pro Gly Thr Asp Tyr

Lys Ile Tyr Leu Tyr Thr Leu Asn Asp Asn Ala Arg Ser Ser Pro Val Val Ile Asp Ala Ser Thr Ala

Ile Asp Ala Pro Ser Asn Leu Arg Phe Leu Ala Thr Thr Pro Asn Ser Leu Leu Val Ser Trp Gln Pro

Pro Arg Ala Arg Ile Thr Gly Tyr Ile Ile Lys Tyr Glu Lys Pro Gly Ser Pro Pro Arg Glu Val Val

Pro Arg Pro Arg Pro Gly Val Thr Glu Ala Thr Ile Thr Gly Leu Glu Pro Gly Thr Glu Tyr Thr Ile

Tyr Val Ile Ala Leu Lys Asn Asn Gln Lys Ser Glu Pro Leu Ile Gly Arg Lys Lys Thr.
```

17. The method of claim 16, wherein said fibronectin fragments comprise a recombinant fibronectin fragment selected from the group consisting of CH-296 and H-296.

18. An improved method of gene transfer into mammalian cells by a replication-defective recombinant retrovirus vector, the improvement comprising conducting the gene transfer without cocultivation, with retrovirus producing cells and in the presence of substantially pure fibronectin, substantially pure fibronectin fragments, or a mixture thereof, so as to increase the frequency of the gene transfer.

19. A cellular composition comprising viable hematopoietic cells transduced by retroviral-mediated gene transfer in the absence of retroviral producer cells and in the presence of an immobilized amount of a polypeptide containing fibronectin, a fibronectin fragment, or a mixture thereof, which provides the binding activity of the Heparin-II binding domain of fibronectin and an amino acid sequence which provides the cell-binding activity of the CS-1 domain of fibronectin, said immobilized amount of polypeptide being effective to increase the frequency of transduction of the hematopoietic cells by the retrovirus vector; said composition also comprising said polypeptide.

20. The cellular composition of claim 19 which is enriched in viable hematopoietic cells wherein said viable hematopoietic cells are stem cells.

21. The cellular composition of claim 19 wherein said viable hematopoietic cells are human hematopoietic cells enriched in human hematopoietic stem cells.

22. The cellular composition of claim 21 which is a substantially homogenous population of human hematopoietic cells characterized as adherent-negative, low density, mononuclear cells.

23. The cellular composition of claim 22 which has been transduced by a recombinant retrovirus vector containing an exogenous gene to correct a protein deficiency or abnormality in the cells.

24. The cellular composition of claim 20 wherein said hematopoietic cells are obtained from umbilical cord blood.

* * * * *